US009872875B2

(12) United States Patent
Ralf et al.

(10) Patent No.: US 9,872,875 B2
(45) Date of Patent: Jan. 23, 2018

(54) COMPONENT AND METHOD FOR TREATING VIRAL DISEASE

(71) Applicant: Institut Pasteur of Shanghai, Chinese Academy of Sciences, Shanghai (CN)

(72) Inventors: Altmeyer Ralf, Shanghai (CN); Peijun Ren, Shanghai (CN)

(73) Assignee: Honz Pharmaceutical Co., Ltd., Haikou, Hainan Province (CN)

( * ) Notice: Subject to any disclaimer, the term of this patent is extended or adjusted under 35 U.S.C. 154(b) by 159 days.

(21) Appl. No.: 14/384,075

(22) PCT Filed: Mar. 11, 2013

(86) PCT No.: PCT/CN2013/072402
§ 371 (c)(1),
(2) Date: Sep. 9, 2014

(87) PCT Pub. No.: WO2013/131496
PCT Pub. Date: Sep. 12, 2013

(65) Prior Publication Data
US 2015/0045318 A1    Feb. 12, 2015

(30) Foreign Application Priority Data
Mar. 9, 2012   (CN) .......................... 2012 1 0062620

(51) Int. Cl.
*A61K 31/7076* (2006.01)
*A61K 31/185* (2006.01)
*A61K 31/675* (2006.01)
*A61K 45/00* (2006.01)
*A61K 31/655* (2006.01)

(52) U.S. Cl.
CPC ........ *A61K 31/7076* (2013.01); *A61K 31/185* (2013.01); *A61K 31/655* (2013.01); *A61K 31/675* (2013.01); *A61K 45/00* (2013.01)

(58) Field of Classification Search
CPC . A61K 31/7076; A61K 31/675; A61K 31/185
USPC .......................................... 514/47, 89, 577
See application file for complete search history.

(56) References Cited

U.S. PATENT DOCUMENTS

2007/0099863 A1* 5/2007 Matute Almau ....... A61K 31/00
                                                        514/47
2011/0263620 A1 10/2011 Hsieh et al.
2012/0045468 A1 2/2012 Chong et al.

FOREIGN PATENT DOCUMENTS

| CN | 101695569 A   | 4/2010 |
| CN | 101780278 A   | 7/2010 |
| CN | 101945655 A   | 1/2011 |
| CN | 102178678 A   | 9/2011 |
| WO | 2009/077559 A2 | 6/2009 |

OTHER PUBLICATIONS

Glossary of medical education terms, Institute of International Medical Education. http://www.iime.org/glossary.htm Accessed in Mar. 2013.*
Ren et al.The approved pediatric drug suramin identified as a clinical candidate for the treatment of EV71 infection—suramin inhibits EV71 infection in vitro and in vivo. Emerg Microbes Infect 3:e62, 2014.*
Arita et al. Characterization of pharmacologically active compounds that inhibit poliovirus and enterovirus 71 infectivity. Journal of General Virology 89:2518-2530, 2008.*
Oberste et al. Molecular Evolution of the Human Enteroviruses: Correlation of Serotype with VP1 Sequence and Application to Picornavirus Classification. J Virol 73:1941-1948, 1999.*
International Search Report issued in PCT/CN2013/072402 mailed on Jun. 20, 2013 (4 pages).
International Search Report and Written Opinion dated May 5, 2015, issued by the Intellectual Property Office of Singapore in corresponding Singapore Patent Application No. 11201405559T (8 pages).
Notification of Reasons for Rejection (Official Action) issued by the Japan Patent Office on Oct. 7, 2015, in related Japanese Patent Application No. JP 2014-560239 (3 pages), with Google English machine translation (3 pages).
Extended European Search Report dated Nov. 2, 2015, issued by the European Patent Office in related European Patent Application No. EP-13757343.2 (6 pages).
Wu, Kan X., et al., "Developments towards antiviral therapies against enterovirus 71"; Drug Discovery Today, 2010, Elsevier Ltd. GBR; vol. 15, No. 23-24, Dec. 2010; XP002746101, ISSN: 1359-6446; pp. 1041-1051.
Tan, Chee Wah, et al., "Enterovirus 71 Uses Cell Surface Heparan Sulfate Glycosaminoglycan as an Attachment Receptor"; Journal of Virology, vol. 87, No. 1, Oct. 24, 2012 (Oct. 24, 2012); XP055220351, US; ISSN: 0022-538X; DOI: 10.1128/JVI.02226-12; pp. 611-620.
Invitation to Respond to 2nd Written Opinion dated Jun. 6, 2016, issued by the Intellectual Property Office of Singapore (IPOS), in related Singaporean Patent Application No. 11201405559T (6 pages).
Notice of Reasons for Rejection (Office Action) dated Jun. 13, 2016, issued by the Japan Patent Office in related Japanese Patent Application No. JP 2014-560239, with Google English machine translation (8 pages).

(Continued)

Primary Examiner — Yih-Horng Shiao
(74) Attorney, Agent, or Firm — Osha Liang LLP

(57) ABSTRACT

A method for treating viral infection includes administering to a subject in need thereof a composition containing P2X receptor antagonists. The methods may achieve preventive or therapeutic effect on hand foot and mouth disease by inhibiting viruses. The P2X receptor antagonists can inhibit infection by a positive-sense single-stranded RNA picornavirus. The virus may be an enterovirus or a Coxsackie virus, such as human enterovirus 71. The P2X receptor antagonist may be PPADS, iso-PPADS, PPNDS, Suramin, NF023, TNP-ATP, NF279, NF157, Evans Blue, an analog thereof, a derivative thereof, or a pharmaceutically acceptable salt thereof.

14 Claims, 25 Drawing Sheets

(56) References Cited

OTHER PUBLICATIONS

Wu, Kan X., et al., "Developments towards antiviral therapies against enterovirus 71"; Drug Discovery Today, vol. 15, No. 23-24, Dec. 2010; pp. 1041-1051.
Hulsmann, Martin, et al., "NF449, a novel picomolar potency antagonist at human P2X1 receptors"; European Journal of Pharmacology, vol. 470, No. 1-2, May 5, 2003; pp. 1-7.
Ishimaru, Yoshiro, et al., "Outbreaks of hand, foot, and mouth disease by enterovirus 71"; Archives of Disease in Childhood, vol. 55, No. 8, May 8, 1980; pp. 583-588.
Licensed practical nurse exam., vol. 51, No. 9, Aug. 2010; pp. 74-75.
SOGO, "Clinic All-Round", vol. 52, Special issue; Mar. 2003; pp. 842-847.
Notice of Reasons for Refusal (Office Action) dated Nov. 14, 2016, issued by the Japan Patent Office in related Japanese Patent Application No. JP-2014-560239, with Google English machine translation (4 pages).
Decision of Final Rejection (Office Action) issued Aug. 12, 2016, by the Korean Intellectual Property Office in related Korean Patent Application No. 10-2014-7027450, with English translation (7 pages).

* cited by examiner

Spinorphin

Leu-Val-Val-Tyr-Pro-Trp-Thr

- $\log_{10}$ EV71 relative titter
- viability x-axis: μM
y-axis (left): $\log_{10}$ relative EV71 titer
y-axis (right): Viability

FIG. 21S bz ATP

- log10 EV71 equvalent genome
- viablity x-axis: μM
y-axis (left): $\log_{10}$ equivalent genome
y-axis (right): Viability

FIG. 21T

COMPONENT AND METHOD FOR TREATING VIRAL DISEASE

CROSS REFERENCE TO RELATED APPLICATIONS

This is a national stage application based on PCT/CN2013/072402, filed on Mar. 11, 2013, which claims priority to Chinese Patent Application No. 201210062620.9, filed on Mar. 9, 2012. This application claims the priority of these prior applications and incorporates their disclosures by reference in their entireties.

BACKGROUND OF INVENTION

Field of the Invention

The present invention belongs to the field of biomedicine. More specifically, the present invention relates to compositions and methods for treating viral diseases.

Background Art

Hand foot and mouth disease (HFMD) is a common viral infection in Western Pacific regions and is a major cause of death and childhood disease in China and Asia. In 2011, there were two million children suffering from HFMD in Western Pacific regions (more than 1.6 million in China, more than 340,000 in Japan, and more than 11 million in Vietnam). In the past 20 years, epidemic outbreak occurred once every two to three years in summer and early autumn in countries having temperate climate (Solomon, Lewthwaite et al. 2010). Chinese mainland has had outbreaks every spring and summer since 2008.

HFMD mainly affects children under five. Major symptoms include mouth ulcers, hand, foot and mouth sores, mouth pain and burning (herpesangina). Most cases show only mild symptoms and are self-limiting. However, there are still a large number of cases (over twenty-seven thousand cases in China in 2010, about 1.6%), which showed severe neurological symptoms, such as aseptic meningitis, encephalitis and polio-like paralysis and central nervous system disorders and neurogenic pulmonary edema and cardiac dysfunction (Huang, Liu et al. 1999; Yang, Wang et al. 2009; Weng, Chen et al. 2010; Rhoades, Tabor-Godwin et al. 2011). 905 and 506 cases of deaths occurred in China in 2010 and 2011, respectively.

HFMD is caused by non-polio enteroviruses. Main pathogenic viruses responsible for HFMD outbreak in Anhui province in 2008 were EV71 and CVA16 (Yan, Gao et al.; Zhang, Wang et al. 2010; Zhu, Zhu et al. 2010). Majority of severe cases and deaths were caused by EV71 infection. EV71 C4 subtype is a major epidemic strain in China, whereas EV71 C1, C2, C4, B3, and B4 subtypes are prevalent in other regions of Asia (Yang, Ren et al. 2009).

HFMD spreads from patients to people by direct contact with mouth and nose discharges, blister fluids, and feces from infected persons (Solomon, Lewthwaite et al. 2010). Infected people are most contagious one week after disease onset, but contagiousness persists even after symptoms were improved (Han, Ma et al. 2010). Many infected people (including most infected adults) do not have symptoms. Children with oral rashes are easier to be diagnosed through clinical and follow-up virology diagnosis.

At present, no HFMD vaccines and drugs are available. The only way to treat patients and to prevent spreading has been hygiene, supportive care, pain relief, mouthwash, and intravenous immunoglobulin (Chinese Ministry of Health 2010). Although vaccines have been in development, protection efficiency, however, still remains unknown, and still requires long period of time for large-scale vaccination to be implemented.

Therefore, there is an urgent need to develop drugs that can prevent and treat HFMD in the field, especially, developing drugs that inhibit EV71 and CVA16 viral infection to achieve prevention and treatment from the source.

SUMMARY OF INVENTION

The object of the present invention is to provide compositions and methods for the treatment of viral diseases.

In a first aspect of the present invention, it provides use of a P2X receptor antagonist for the preparation of compositions for inhibiting positive-sense single-stranded RNA picornavirus.

In a preferred embodiment, the P2X receptor antagonist is used for the preparation of compositions for preventing, alleviating, or treating HFMD.

In another preferred embodiment, the compositions are also used for: systemic administration or parenteral administration; preferably, the compositions are used for oral administration, intravenous injection, intramuscular injection, or inhalation.

In another aspect of the present invention, it provides a method for inhibiting positive-sense single-stranded RNA picornavirus, including: administering to a subject in need thereof an effective amount of P2X receptor antagonists.

In a preferred embodiment, the objects are mammals infected by viruses, including human, monkeys, or mice, etc. infected by enterovirus 71 or Coxsackie virus, preferably, the subject having HFMD.

In another preferred embodiment, the P2X receptor antagonist is selected from the group consisting of: PPADS, iso-PPADS, PPNDS, Suramin, NF023, TNP-ATP, NF279, NF157, Evans Blue, and/or analogs thereof or derivatives thereof, and/or pharmaceutically acceptable salts thereof.

In another preferred embodiment, the virus is enterovirus.

In another preferred embodiment, the virus is enterovirus A.

In another preferred embodiment, the virus is human enterovirus 71 and Coxsackie virus.

More preferably, the virus is human enterovirus 71, C4 subtype and Coxsackie virus A16 subtype.

Due to the disclosure herein, other aspects of the present invention will be apparent to those skilled in the art.

BRIEF DESCRIPTION OF DRAWINGS

FIG. 1A shows the mean values of three results.

FIG. 20A shows inhibition by NF279. FIG. 20B shows inhibition by Evans Blue. FIG. 20C shows inhibition by NF157. FIG. 20D shows inhibition by iso-PPDAS. FIG. 20E shows inhibition by NF023. FIG. 20F shows inhibition by PPADS.

FIG. 21A shows inhibition by NF110. FIG. 21S shows inhibition by Spinophin. FIG. 21T shows inhibition by bz ATP. FIG. 21X shows inhibition by MRS 2219.

DETAILED DESCRIPTION

Figures 1A, 1B:
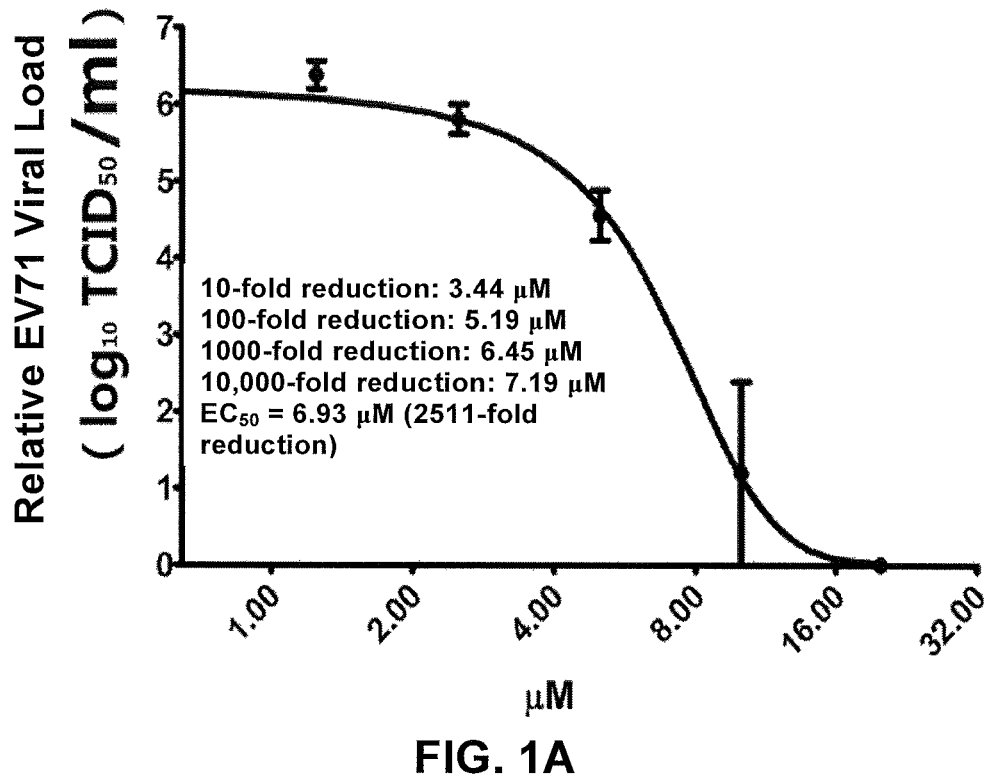
FIG. 1A shows, at different E02 concentrations, EV71 clinical isolates were used to infect RD cells, at an MOI of 0.1. After incubation for 46 h, viral RNA in culture supernatant was extracted. Relative EV71 viral load was determined by quantitative RT-PCR. Numbers in columns 2, 3, 4 of the table (FIG. 1B) represent results obtained from three repeated tests.

After intensive studies, the present inventors revealed, for the first time, a new use of P2X receptor antagonists for the preparation of viral compositions. The P2X receptor antagonists achieve preventive or therapeutic effect on HFMD by inhibiting viruses.

P2X receptor antagonists and use thereof

P2X is a class of ATP-gated ion channel family of proteins expressed on cell membrane, and is usually a homologous or heterologous trimer formed by an extracellular domain, two transmembrane domains, and two intracellular domains. P2X family includes seven subtypes. Triggered by extracellular ATP, P2X ion channels open, causing calcium ion influx and intracellular calcium accumulation. A series of downstream signal transduction is activated through MAPK, PKC, and calmodulin (Erb, Liao et al. 2006).

After in-depth study, the present inventors found that some P2X receptor antagonists are useful for inhibiting viruses. The viruses are those of positive-sense single-stranded RNA picornavirus family, including Aphthovirus, Avihepatovirus, Cardiovirus, Theilovirus, Enterovirus, Erbovirus, Hepatovirus, Kobuvirus, Parechovirus, etc.; preferably, the virus is Enterovirus, including Enteroviruses A-H class, Rhinovirus A-C; preferably, the virus is Enterovirus A, including Baboon enterovirus, human Coxsackie virus type A2-8, A10, A12, A14, A16, human enterovirus type 71, 76, 89, 90-92, etc.; preferably, including Enterovirus 71 (EV71) (including A, B, and C subtypes), Coxsackie viruses (including classes A and B, preferably, including A16 subtype; CVA16).

It is known that enterovirus 71 or Coxsackie virus A16 infection is a major cause of HFMD. Studies published by Chinese Ministry of Health "Hand Foot and Mouth Disease Treatment Guidelines (2010 version)" and a number of published studies all indicate that EV71 and CVA16 are major pathogens. Therefore, P2X receptor antagonists can be used for preventing and treating HFMD.

As an alternative embodiment of the present invention, the P2X receptor is P2X1-7 receptor subtypes.

As another preferred embodiment of the present invention, the P2X receptor antagonist is selected from: PPADS, Iso-PPADS, PPNDS, Suramin, NF023 (Suramin derivative), TNP-ATP, NF279, NF 157, and Evans Blue.

In another more preferred embodiment of the present invention, the P2X receptor antagonist may be: Suramin, PPADS, iso-PPADS, PPNDS, NF023, NF279, TNP-ATP, NF157, and Evans Blue.

The present invention also includes isomers of various compounds exemplified above, racemates, pharmaceutically acceptable salts, hydrates, precursors, derivatives or analogs thereof, so long as the isomers, racemates, pharmaceutically acceptable salts, hydrates, derivatives or analogs also possess the function of inhibiting viruses (e.g. enterovirus 71 or Coxsackie virus A16 subtype).

The term "isomer" includes: conformational isomers, optical isomers (e.g., enantiomers and non-enantiomers), geometric isomers (e.g., cis and trans isomers).

The term "derivative or analog" refers to P2X receptor antagonists having similar structural formula as exemplified above, in particular, those having same core structure, but compounds having some of radicals substituted with similar radicals. The compounds still maintain the function of inhibiting viruses (such as enterovirus 71 or Coxsackie virus A16 subtype). For example, H is substituted with C1-C4 alkyl; C1 alkyl is substituted with C2 alkyl; substitutions occur between halogen group members (including F, Cl, Br, and I); and substitutions occur between OH, $OCH_3$, $OCH_2CH_3$, $OCH_2CH_3$, etc.

The term "pharmaceutically acceptable salts" refers to salts formed by reacting the above-mentioned compounds with inorganic acid, organic acid, alkali metals or alkaline earth metals. These salts include (but are not limited to): (1) salts formed with the following inorganic acids: such as hydrochloric acid, hydrobromic acid, hydroiodic acid, sulfuric acid, nitric acid, phosphoric acid; (2) salts formed with the following organic acids, such as acetic acid, lactic acid, citric acid, succinic acid, fumaric acid, gluconic acid, benzoic acid, methane sulfonic acid, ethane sulfonic acid, benzene sulfonic acid, p-toluene sulfonic acid, oxalic acid, succinic acid, tartaric acid, maleic acid, or arginine Other salts include salts formed with alkali metals or alkaline earth metals (e.g., sodium, potassium, calcium, or magnesium), ammonium salts or water-soluble amine salts (e.g. N-methylglucamine salt), lower alkanol ammonium salts and other pharmaceutically acceptable amine salts (e.g., methylamine salts, ethylamine salts, propylamine salts, dimethylamine salts, trimethylamine salts, diethylamine salts, triethylamine salts, tert-butylamine salts, ethylenediamine salts, hydroxyethyl amine salts, di-hydroxyethylamine salts, tris-hydroxyethyl amine salts, and ammonium salts formed, respectively, with morpholine, piperazine, lysine) or other conventional form of "prodrug." Compounds have one or more asymmetric centers. Thus, these compounds may exist as racemic mixtures, individual enantiomers, individual non-enantiomers isomers, non-enantiomer mixtures, cis or trans isomers.

The term "precursor compound" refers to precursor compounds, after being administered by appropriate methods, metabolized or reacted chemically in patients, are converted to P2X receptor antagonist compounds or salts formed with or solutions of P2X receptor antagonist compounds, as exemplified previously in the present invention. Precursor compounds include, but are not limited to, forms of carboxylic acid esters, carbonic esters, phosphate esters, nitric acid esters, sulfuric acid esters, sulfone esters, sulfoxide esters, amides, carbamates, azo compounds, phosphorus amide, glucoside, ether, acetals, etc.

Drug Screening Methods

The present inventors found a class of P2X receptor antagonists can inhibit viral replication. Such an inhibitory effect is achieved possibly by targeting P2X receptors.

After knowing that P2X receptor antagonists can selectively bind to P2X receptors to induce virus inhibitory effect, substances binding to P2X receptors can be screened based on these characteristics. After that, truly useful drugs for inhibiting viruses can be found from the afore-mentioned substances.

Accordingly, the present invention provides methods of screening potential drugs for the prevention and the treatment of HFMD, the methods include: (1) providing a system containing (e.g., expressing) P2X receptors; (2) providing candidate substances to the system of step (1), observing the binding status of candidate substances to P2X receptors. If candidate substances can bind to P2X receptors, the candidate substances are potential drugs for preventing and treating HFMD. The system containing (e.g., expressing) P2X receptors may be, for example, a cell system. The cells may be those expressing endogenous P2X receptors or those engineered to express P2X receptors. The systems containing P2X receptors may also be subcellular systems, solution systems, tissue systems, organ systems or animal systems (such as animal models, preferably non-human mammalian animal models, such as mice, rabbits, sheep, monkeys, etc.), etc. Techniques for detecting whether or not a compound binds to receptors or receptor subunits are known in the art.

In a preferred embodiment of the present invention, during screening, to more easily observe the differences of P2X receptors binding to candidate substances, control group may be set up. The control group may be systems containing P2X receptors without adding candidate substances.

The candidate substances may include (but are not limited to): small molecule compounds, polypeptides, and ligands. Preferably, the candidate substances are small molecule compounds. For example, the candidate substances may be various P2X receptor antagonists.

As a preferred embodiment of the present invention, the methods further include: performing further cell experiments and/or animal testing on the obtained potential substances to further select and determine truly useful substances for inhibiting viruses.

In another aspect, the present invention also includes substances for inhibiting viruses obtained by the screening methods.

Compositions

Compounds of the present invention may be used to prepare pharmaceutical compositions. Pharmaceutically acceptable carriers can be solid or liquid. Solid formulations include powders, tablets, pills, capsules, wafers, suppositories, and dispersible granules. Solid carriers can be one or several substances, which may serve as diluents, flavoring agents, binders, preservatives, tablet disintegrating agents, or encapsulating materials. In powders, carriers are micro-segmented solids. Compounds of the present invention and micro-segmented active ingredients are present in mixture. In tablets, such compounds are mixed with required adhesive carriers at suitable ratios and compacted in desired shapes and sizes. Suitable carriers are magnesium carbonate, magnesium stearate, talcum, sugar, lactose, pectin, dextrin, starch, gelatin, carboxymethyl cellulose, sodium carboxymethyl cellulose, low melting wax, and cocoa butter, etc. Similarly, wafers or lozenge, tablets, powders, capsules, and pills. Wafers and lozenges may be solid formulations suitable for oral administration.

Liquid preparations include solutions, suspensions, and emulsions, for example, water or aqueous propylene glycol solutions. For non-parenteral injection liquid preparations can be prepared in aqueous polyethylene glycol solutions. Aqueous solutions suitable for oral administration can be prepared by dissolving active components in water and, as required, adding suitable colorants, flavoring agents, emulsifiers, and thickeners.

The compositions can be used for systemic administration, local administration, or parenteral administration.

Aqueous suspensions suitable for oral administration can be prepared by dispersing micro-segmented active ingredients in aqueous viscous materials, such as natural or synthetic gums, resins, methylcellulose, sodium carboxymethylcellulose, and other well-known suspensions.

In therapeutic use, daily initial dose of compounds used in the present invention is at 0.01-200 mg/kg body weight, more preferably 0.25-100 mg/kg body weight, more preferably 0.5-50 mg/kg body weight. However, these doses may be changed based on patients' need and severity of diseases being treated and compounds being used. Generally speaking, treatments begin with smaller doses than the optimum doses of the compounds, after which this dose is increased in small amount until reaches the best results. For the sake of convenience, if desired, total daily dose may be divided into several doses for administration in a day.

Pharmaceutical compositions of the present invention may also be simultaneously used in combination with other therapeutic agents or adjuvant.

Kits

The P2X receptor antagonists of the present invention or compositions containing P2X receptor antagonists may be placed in kits convenient for sale or for use.

The P2X receptor antagonists or compositions containing P2X receptor antagonists may be prepared in the form of unit doses to be placed in kits. "Unit dose form" refers to, for the convenience of administration, the dose form required for single administration prepared by using P2X receptor antagonists of the present invention or compositions containing P2X receptor antagonists, includes, but is not limited to, various solid dose forms (e.g. tablets), liquids, capsules, and controlled release formulations. Once unit dose forms are prepared, 1-3 doses of the unit dose forms of compositions may be administered daily.

The kits also include: dosing instructions for the administration of P2X receptor antagonists to subjects in need of viral inhibition (such as patients suffering from viral diseases or places containing viruses) so that people would know how to take medication correctly.

The present invention is further illustrated in combination with the following specific embodiments. It should be understood that these embodiments are merely used to illustrate the present invention and are not intended to limit the scope of the present invention. Specific conditions in experimental methods not indicated in the following embodiments are usually those described according to conventional conditions, such as that described in Sambrook, J. et al., Molecular Cloning, A Laboratory Manual, Science Press, 2002, or according to the conditions recommended by manufacturers. Unless otherwise indicated, percentages and parts are calculated based on volume.

I. EXPERIMENTAL MATERIALS

1. Cell Lines

Rhabdomyosarcoma cells (RD cells) were purchased from ATCC, Cat No. VR-805. Cell culture medium was DMEM containing 10% (v/v) FBS, and 1% (w/v) ampicillin/streptomycin solution was added.

2. Virus Strains

EV71 clinical isolates: EV71 FY 573, isolated from HFMD samples in Anhui Province, China, 2008; genotype EV71 C4; Genbank accession number HM 064456; provided by Shanghai Institutes for Biological Sciences, Chinese Academy of Sciences.

EV71 clinical isolates SH-TS and SH-RS, provided by Shanghai Institutes for Biological Sciences, Chinese Academy of Sciences, genotype C4.

EV71 clinical isolates SEP-4, provided by and isolated from Cambodia clinical HFMD samples by Institut Pasteur of Cambodia, genotype C4.

EV71-FY23 strain: provided by Virology and Immunology Unit, Institute of Medical Biology, Chinese Academy of Medical Sciences, batch number: 20121001, Genebank accession number EU812515.1.

EV71 M.A.V.: EV71 mouse-adapted strain, obtained by repeated passage of EV71 FY 573 in newborn mice.

CVA16: Coxsackie A16 virus subtype, shzh05-1 (GenBank # EU262658).

3. Compounds

E02 was purchased from Sigma-Aldrich, administered as Suramin Sodium.

Suramin used in monkey experiments was provided by Bayer, administered as Suramin free acid.

iso-PPADS (0683-10 mg), NF 279 (1199-10 mg), and PPNDS (1309) were purchased from Tocris.

Unless otherwise indicated, other compounds were purchased from Sigma-Aldrich and Tocis.

4. Rt-PCR Primers and Probes (5' to 3')

```
EV71 forward primer:
                                       (SEQ ID NO: 1)
CCCTGAATGCGGCTAATC;

EV71 reverse primer:
                                       (SEQ ID NO: 2)
ATTGTCACCATAAGCAGCCA;

EV71 probe:
                                       (SEQ ID NO: 3)
FAM (6-carboxy fluorescein)-AACCGACTACTTTGGGTGTCC GTGTTTC-TAMRA (6-carboxy-tetramethyl-rhodamine);

GAPDH forward primer:
                                       (SEQ ID NO: 4)
GAAGGTGAAGGTCGGAGTC;

GAPDH reverse primer:
                                       (SEQ ID NO: 5)
GAAGATGGTGATGGGATTTC;

P2X1-164F:
                                       (SEQ ID NO: 6)
CCTCTTCGAGTATGACACC;

P2X1-164R:
                                       (SEQ ID NO: 7)
CAGAGACACTGCTGATGAG;

P2X2-202F:
                                       (SEQ ID NO: 8)
CTGGACATGCTGGGAAACG;

P2X2-202R:
                                       (SEQ ID NO: 9)
TGCCCTTGGAGAAGTGGAAT;

P2X3-153F:
                                       (SEQ ID NO: 10)
GGCTCGACAGCGTTTCT;

P2X3-153R:
                                       (SEQ ID NO: 11)
TGCCAGCATTCCCGTAT;

P2X4-201F:
                                       (SEQ ID NO: 12)
TGGGATGTGGCGGATTAT;
```

-continued

P2X4-201R:
(SEQ ID NO: 13)
TACGCACCTGCCTGTTGAGA;

P2X5-220F:
(SEQ ID NO: 14)
TCTTTGCCTGGTGCCCGTTG;

P2X5-220R:
(SEQ ID NO: 15)
ATCACGGAGCCCAGTCGGAAG;

P2X6-205F:
(SEQ ID NO: 16)
GGAGGACAAAGTATGAGGAGG;

P2X6-205R:
(SEQ ID NO: 17)
GAATGGGTTGGCAAGTGG;

P2X7-175F:
(SEQ ID NO: 18)
CGTGGAGAAGTGAAGAAG;

P2X7-175R:
(SEQ ID NO: 19)
TCGGTCAGAGGAACAGAGC.

5. Reagents and Kits

DMEM: Invitrogen cat#11965118;
FBS: Invitrogen cat#10099141;
TRYPSIN 0.25% EDTA: Invitrogen cat#525200072;
Viral RNA extraction kit: QIAamp Viral RNA Mini Kit, QIAGEN cat#52906;
Cell total RNA extraction kit: RNeasy Mini Kit (250), QIAGEN cat#74106;
Tissue preservation solution: RNAstore sample preservation solution, Tiangen Technology (Beijing) Co. DP408-02;
Tissue RNA extraction kit: RNAprep pure animal tissue total RNA extraction kit, Tiangen Technology (Beijing) Co., DP43;
Taqman real time RT-PCR reagent: ABI taqMan® One-Step RT-PCR, ABI cat #4309169;
SYBR real time RT-PCR reagent: QIAGEN QuantiTect SYBR Green RT-PCR Kit (200), Cat #204243;
One-step RT-PCR reagents: QIAGEN OneStep RT-PCR Kit (100); Cat #201212;
DNA electrophoresis agarose: Biowest Argarose, Cat # BW-R0100;
DNA marker: DL2,000 DNA Marker, Cat # D501;
Crystal violet: Santa Cruz cat # sc-207460;
Seaplaque Agarose: lonza/amaxa 4 50101;
CellTiter Glo: Promega G7572;
PENICILLIN STREPTOMYCIN: Invitrogen Cat #15140122.

6. Abbreviations

CPE: cytopathic effect,
CT: cycle threshold,
$EC_{50}$: 50% effective concentration,
EV71: Enterovirus 71,
Evans Blue: 6,6-[(3,3'-Dimethyl[1,1'-biphenyl]-4,4'-diyl)bis (azo)bis[4-amino-5-hydroxy-1,3-naphthalenedisulphonic acid]tetrasodium salt;
HFMD: Hand Foot and Mouth Disease,
iso-PPADS: pyridoxal-phosphate-6-azophenyl-2',5'-disulphonic acid;
M.A.V.: Mouse Adapted Virus,
MAPK: Mitogen-activated protein kinases,
MOI: Multiplicity of infection,
NF 023: 8,8'-[carbonylbis(imino-3,1-phenylenecarbonylimino)]bis-1,3,5-naphthalene-trisulphonic acid, hexasodium salt;
NF 157: 8,8'-[Carbonylbis[imino-3,1-phenylenecarbonylimino(4-fluoro-3,1-phenylene) carbonylimino]];
NF 279: 8,8'-(carbonylbis(imino-4,1-phenylenecarbonylimino-4,1-phenylenecarbonylimino))bis(1,3,5-naphthalenetrisulfonic acid)
PFU: plaque forming unit
PKC: Protease kinase C,
PPADS: pyridoxal-phosphate-6-azophenyl-2', 4'-disulphonic acid;
PPNDS: Pyridoxal-5'-phosphate-6-(2'-naphthylazo-6'-nitro-4',8'-disulfonate) tetrasodium salt,
RD cell: Rhabdomyosarcoma cell,
TOA: Time of Addition assay,
$TCID_{50}$: 50% Tissue Culture Infective dose,
TNP-ATP: trinitrophenol-ATP,
UTP: uridine triphosphate, 7. Compound Structure and Cas Numbers

| Compound | Structure | CAS Registration Number or Chemical Formula |
|---|---|---|
| E02 | 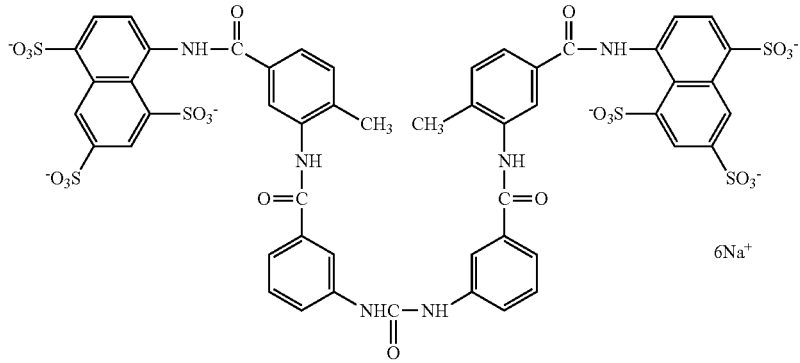 | CAS: 129-46-4 |

-continued
| Compound | Structure | CAS Registration Number or Chemical Formula |
|---|---|---|
| iso-PPADS | 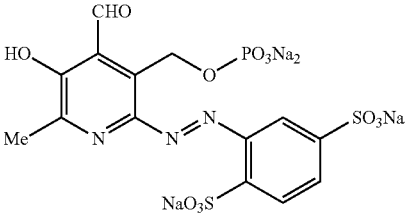 | chemical formula: $C_{14}H_{10}N_3Na_4O_{12}PS_2$ |
| NF023 | 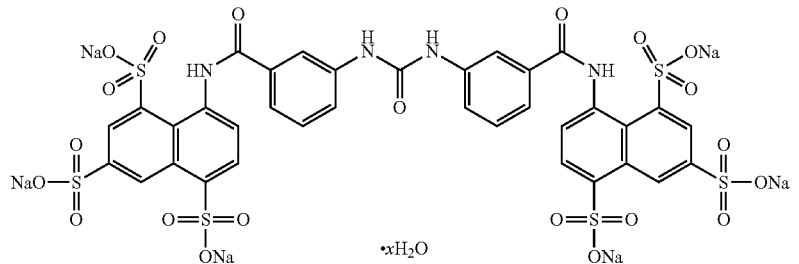 | CAS: 104869-31-0 (hydrated) |
| NF279 | 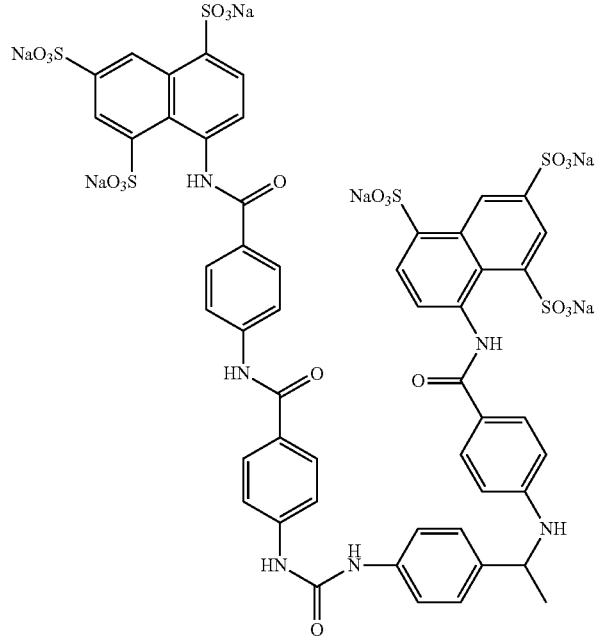 | CAS: 202983-32-2 |
| PPADS | 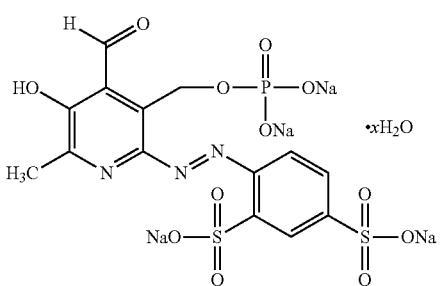 | CAS: 192575-19-2 (Tetrasodium salt hydrate) |

-continued
| Compound | Structure | CAS Registration Number or Chemical Formula |
|---|---|---|
| TNP-ATP | 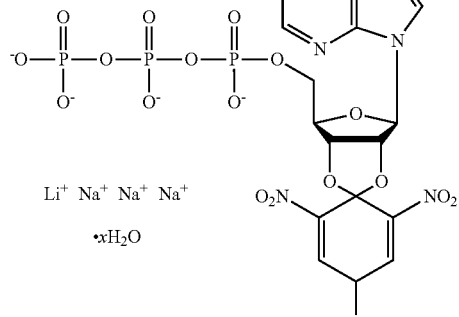 | CAS: 61368-63-6 |
| PPNDS | 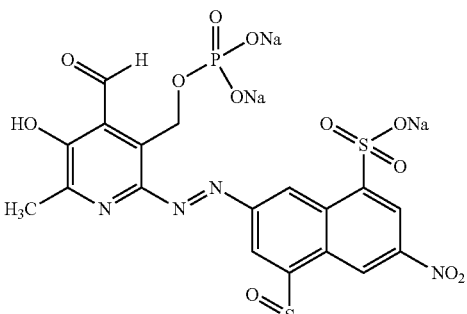 | chemical formula: $C_{18}H_{11}N_4Na_4O_{14}PS_2$ |
| NF 157 | 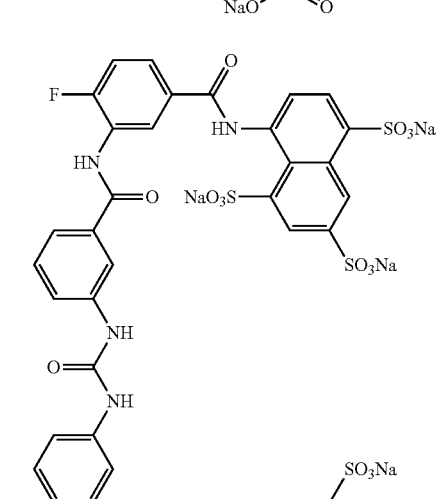 | 104869-26-3 |

| Compound | Structure | CAS Registration Number or Chemical Formula |
|---|---|---|
| Evans Blue | [chemical structure] | 314-13-6 |

II. EMBODIMENTS

EV71 and CVA16 are major pathogens of HFMD. In the following examples, the present inventors determined the ability of E02 (Suramin Sodium) or the analogs thereof to inhibit EV71 and CVA16 infection in vitro and in vivo.

Example 1

E02 Inhibits EV71 Clinical Isolate (EV71 FY 573) Infection of RD Cells (In Vitro Tests)

1. E02 can Inhibit EV71 Replication in RD Cells

RD cells were infected with EV71 clinical isolate (EV71 FY 573) in different E02 concentrations, at the MOI (multiplicity of infection) of 0.1. At 46 h post infection, viral RNA in culture supernatant was extracted, and the relative EV71 viral load was determined by quantitative RT-PCR. Procedures are detailed as follows:

① Cell seeding: 24 h prior to infection, RD cells were seeded in 96-well cell culture plates, $5 \times 10^4$ cells per well.

② Infection:
a. Virus pre-incubated with drug: virus stock solution was diluted to $5 \times 10^4$ $TCID_{50}$/ml with DMEM and dispensed to 96-well plates at 100 μl per well, and 11 μl of E02 dissolved in DMEM at corresponding concentration or DMEM was added, and incubated at 37° C. for 1 h;
b. Cells pre-incubated with drug: cell culture medium was removed from 96-well plates, each well was added 100 μl of DMEM, then added 11 μl of E02 solution at corresponding concentration or DMEM, and incubated at 37° C. for 1 h;
c. After 1 h incubation, drug was discarded from cell culture plates, 111 μl of virus pre-incubated with drug was transferred to cell culture plates, and incubated at 37° C. for 1 h;
d. After incubation, the supernatant was discarded, cells were washed twice with 50 μl of DMEM, each well was added 180 μl of DMEM containing 2% FBS, 20 μl of E02 solution at corresponding concentration or DMEM. Cell culture plates were placed in 37° C., 5% (v/v) carbon dioxide incubator for incubation.

③ Harvesting virus and RNA extraction: after infection, cells were cultured for 46 h, 140 μl of supernatant was transferred to 96-deep well plates, viral RNA extraction was performed using viral RNA extraction kit (QIAGEN QIAamp Viral RNA Mini Kit, cat #52906) according to standard operating procedures of the kit.

④ Viral load measurements: EV71 5'UTR gene was detected using ABI Taqman one-step RT-PCR kit (ABI TaqMan® One-Step RT-PCR, cat #4309169) of ABI 7900HT 384-well plates PCR system. Reaction systems and PCR program are shown in Table 1 and Table 2. EV71 5'UTR quantitative RT-PCR thermal cycling program (Taqman);

⑤ PCR CT values were converted to viral load using PCR standard curves (standard curves were obtained by CT values determined by performing RT-PCR on RNA extracted from viruses serially diluted with defined titers at 10-fold).

TABLE 1

EV71 5'UTR real-time quantitative RT-PCR reaction system (Taqman)
Total reaction volume: 10 μl
PCR reagent Cat#ABI4309169
TaqMan ® One-Step RT-PCR

| | |
|---|---|
| 2 × reaction buffer | 5 μl |
| 40 × RNase inhibitor | 0.25 μl |
| Forward primer 3 μM | 1 μl |
| Reverse primer 9 μM | 1 μl |
| Probe 1.5 μM | 1 μl |
| Viral RNA sample | 1.75 μl |

TABLE 2

EV71 5'UTR quantitative RT-PCR thermal cycling program (Taqman)
PCR thermal cycling program
ABI 7900HT 384

| | |
|---|---|
| 1. 48° C. | 30 min |
| 2. 95° C. | 10 min |
| 3. 95° C. | 15 sec |
| 4. 60° C. | 1 min |
| In which, repeat perform steps 3-4 for 40 cycles | |

The results show E02 can inhibit EV71 replication in RD cells. $EC_{50}$ (50% effective concentration) is 6.93 μM. At 3.44 μM, EV71 replication can be reduced for 10-fold. At 5.19 μM, EV71 replication was reduced for 100-fold; at 6.45 μM, 1,000-fold reduction, and at 7.63 μM, 10,000-fold reduction, see FIGS. 1A-B.

2. E02 Significantly Reduces EV71 $TCID_{50}$ in RD Cells

EV71 (clinical isolate EV71 FY 573) in 10-fold serial dilutions was used to infect RD cells at different E02 concentrations. After 3-4 days of incubation, CPE (cytopathic effect) was observed under optical microscope and stained with crystal violet to calculate 50% tissue culture infective dose. Procedures are detailed as follows:

① Cell seeding: 24 h prior to infection, RD cells were seeded in 96-well cell culture plates, $5 \times 10^4$ cells per well.

② Infection:
a. Virus pre-incubated with drug: virus stock solution was in 10-fold serial dilution with DMEM and dispensed to 96-well plates at 100 μl per well, and 11 μl of E02 dissolved in DMEM at corresponding concentration was added, and incubated at 37° C. for 1 h;

b. Cells pre-incubated with drug: cell culture medium was removed from 96-well plates, each well was added 100 μl DMEM, then added 11 μl of E02 solution at corresponding concentration, and incubated at 37° C. for 1 h;

c. After 1 h incubation, drug was discarded from cell culture plates, 111 μl of virus pre-incubated with drug was transferred to cell culture plates, and incubated at 37° C. for 1 h;

d. After incubation, virus and drug mixture was removed, cells were washed twice with 50 μl of DMEM, each well was added 180 μl of DMEM containing 2% FBS, 20 μl of E02 solution at corresponding concentration, cell culture plates were placed in 37° C., 5% (v/v) carbon dioxide incubator for incubation.

③ After cultured for 3-4 days, CPE was observed under optical microscope, and stained with crystal violet, $TCID_{50}$ was calculated using Reed-Muench method.

Figure 2:
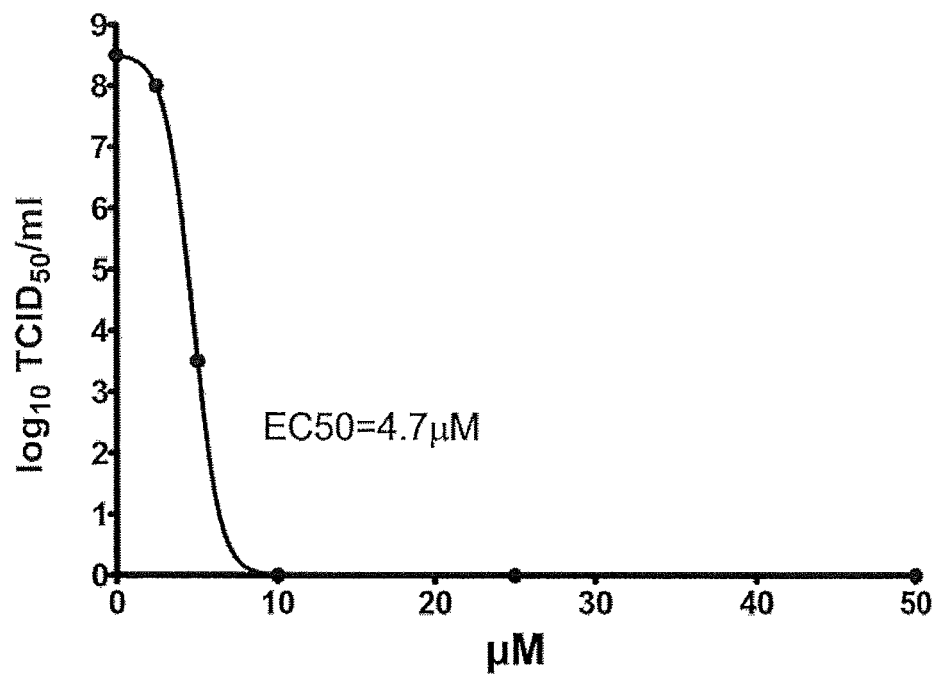
FIG. 2 shows, at different E02 concentrations, EV71 in 10-fold serial dilutions were used to infect RD cells. After incubation for 3-4 days, CPE (cytopathic effect) was observed under optical microscope and stained with crystal violet to calculate 50% tissue culture infective dose ($TCID_{50}$).

The results show E02 can inhibit CPE caused by EV71 infection in RD cells. The $EC_{50}$ of E02 to reduce EV71 $TCID_{50}$ in RD cells is 4.7 μM, see FIG. 2. Therefore, E02 significantly reduces EV71 $TCID_{50}$ in RD cells.

3. E02 Reduces EV71 Plaque Forming Units in RD Cells

EV71 (clinical isolate of EV71 FY 573) was used to infect RD cells cultured in 12-well plates at different E02 concentrations. After cultured for 5 to 7 days, stained and plaque forming units were calculated. Procedures are detailed as follows:

① Cell seeding: 24 h prior to infection, RD cells were seeded in 12-well cell culture plates, $2\times10^5$ cells per well.

② Infection of cells:

a. Virus pre-incubated with drug: virus stock solution was in 10-fold serially diluted with DMEM to 50,000 PFU/ml, 5,000 PFU/ml, and 500 PFU/ml; and dispensed to 12-well plates at 500 μl per well, and 56 μl of E02 dissolved in DMEM at corresponding concentration was added, and incubated at 37° C. for 1 h;

b. Cells pre-incubated with drug: cell culture medium was removed from 12-well plates, each well was added 500 μl DMEM, then added 56 μl of E02 solution at corresponding concentration, and incubated at 37° C. for 1 h;

c. After 1 h incubation, drug was discarded from cell culture plates, 556 μl of virus pre-incubated with drug was transferred to cell culture plates, and incubated at 37° C. for 1 h;

d. After incubation, virus and drug mixture were removed, cells were washed twice with 300 μl of DMEM, each well was added 150 μl of DMEM containing corresponding concentration of E02, and was added 1350 μl of pre-heat melted (cooled to 37~40° C.) DMEM containing 1% low-melting seaplaque, 2% FBS. Cell culture plates were placed in 37° C., 5% (v/v) carbon dioxide incubator for incubation.

③ After cultured for 5-7 days, gels were removed, stained with crystal violet, washed once with PBS, plaque numbers recorded and plaque forming units calculated.

Figure 3:
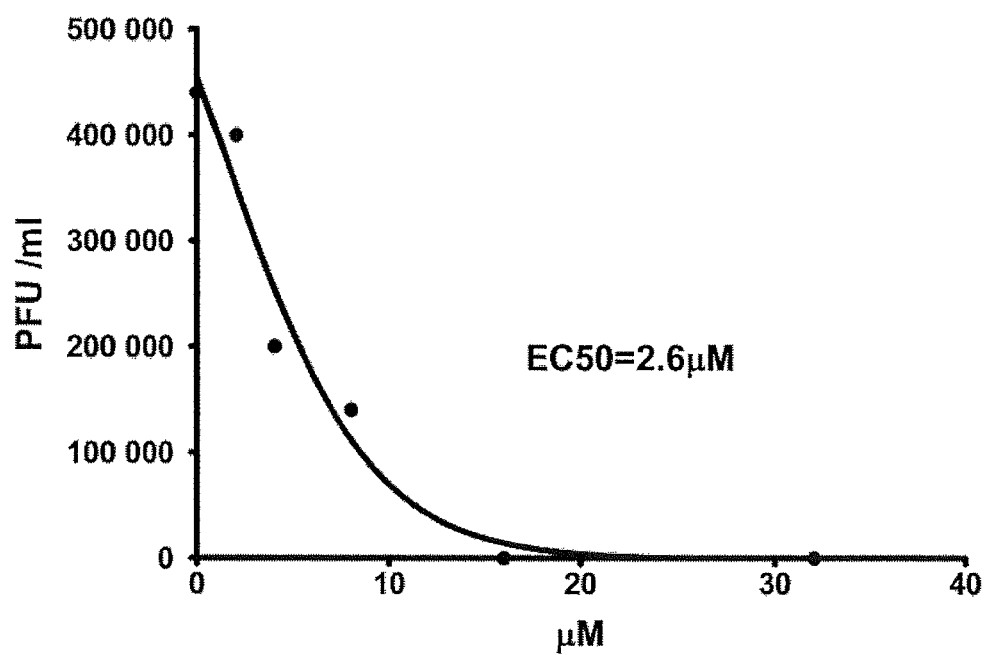
FIG. 3 shows, at different E02 concentrations, EV71 was used to infect RD cells cultured in 12-well plates. After incubation for 5-7 days, stained and plaque-forming units (PFU) were calculated.

The results show E02 can reduce the number of plaques formed by EV71 in RD cells. $EC_{50}$ of E02 to reduce EV71 PFU in RD cells is 2.6 μM, see FIG. 3. Therefore, E02 can reduce EV71 plaque forming units in RD cells.

In summary, through three test methods: real-time quantitative RT-PCR, $TCID_{50}$ and PFU, the results show E02 can inhibit EV71 clinical isolate infection of RD cells: $EC_{50}$ of inhibiting EV71 replication in RD cells is 6.93 μM; $EC_{50}$ for reducing $TCID_{50}$ in RD cells is 4.7 μM; $EC_{50}$ for reducing PFU is 2.6 μM.

Example 2

E02 Inhibits EV71 Mouse Adapted Strain Infection in RD Cells (in Vitro Tests)

1. E02 Reduces EV71 M.a.V. $TCID_{50}$ in RD Cells

EV71 M.A.V. in 10-fold serial dilutions was used to infect RD cells at different E02 concentrations. After cultured for 3-4 days, CPE was observed under optical microscope, and stained with crystal violet, to calculate 50% tissue culture infective dose. Specific steps are similar to that for testing corresponding $TCID_{50}$ of Example 1.

Figure 4:
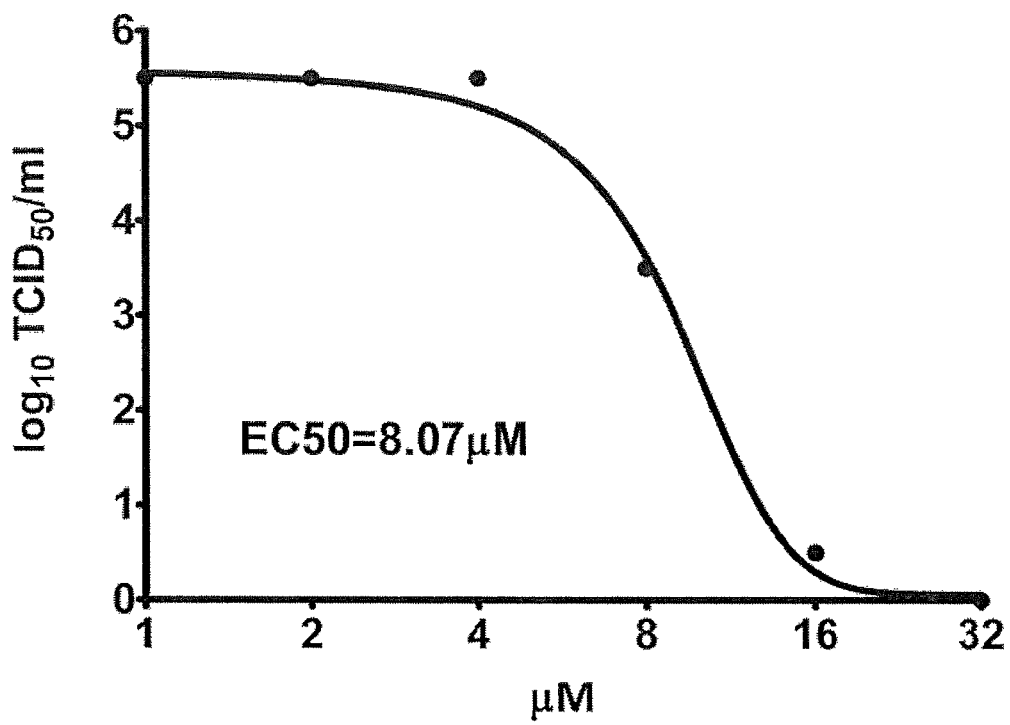
FIG. 4 shows, at different E02 concentrations, EV71 M.A.V. in 10-fold serial dilutions was used to infect RD cells. After incubation for 3-4 days, CPE was observed under optical microscope and stained with crystal violet to calculate 50% tissue culture infective dose (TCID$_{50}$).

The results show the EC50 of E02 to reduce EV71 M.A.V. $TCID_{50}$ in RD cells is 8.07 μM, see FIG. 4. Therefore, E02 reduces EV71 M.A.V. $TCID_{50}$ in RD cells.

2. E02 Reduces EV71 M.a.V. PFU in RD Cells

EV71 M.A.V. was used to infect RD cells cultured in 12-well plates at different E02 concentrations. After cultured for 5 to 7 days, stained and plaque-forming units were calculated. Detailed procedures were the same as the corresponding PFU testing method of Example 1.

Figure 5:
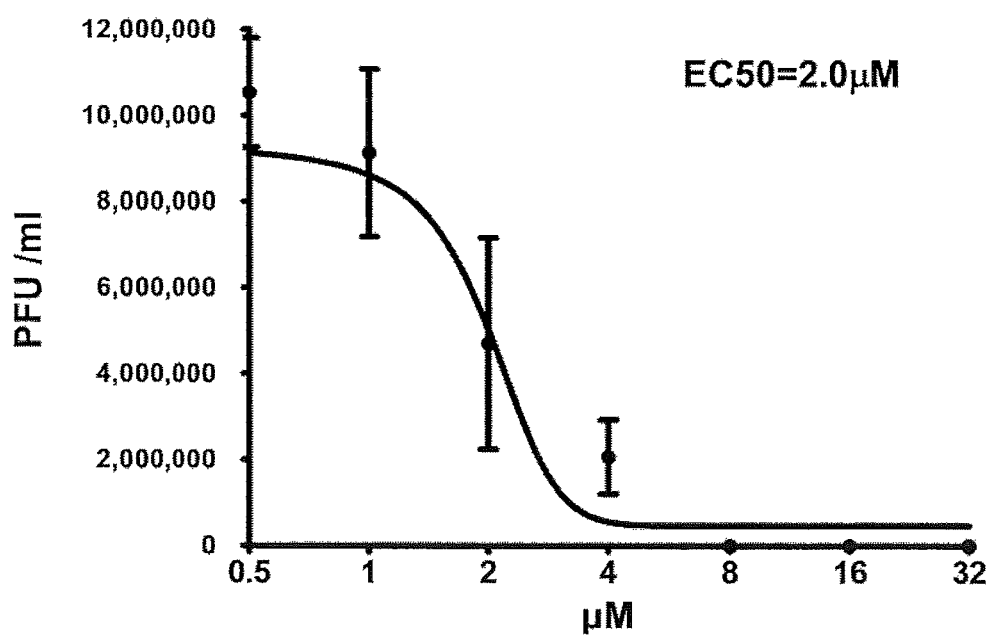
FIG. 5 shows, at different E02 concentrations, EV71 M.A.V. was used to infect RD cells cultured in 12-well plates. After incubation for 5-7 days, stained and plaque-forming units (PFU) were calculated.

The $EC_{50}$ of E02 to reduce EV71 M.A.V. PFU in RD cells is 2.0 μM, see FIG. 5. Therefore, E02 reduces EV71 M.A.V. PFU in RD cells.

In summary, $TCID_{50}$ and PFU tests show E02 can inhibit the infection in RD cells caused by EV71 mouse adapted strain with $EC_{50}$ of 8.07 μM and 2.0 μM, respectively.

Example 3

E02 Inhibit Coxsackie Virus A16 (CVA16) Infection in RD Cells (In Vitro Tests)

Coxsackie virus A16 in 10-fold serial dilutions were used to infect RD cells at different E02 concentrations. After cultured for 2 days, CPE was observed under optical microscope, and stained with crystal violet, to calculate 50% tissue culture infective dose. Specific procedures were the same as the $TCID_{50}$ testing method of Example 1.

Figure 6:
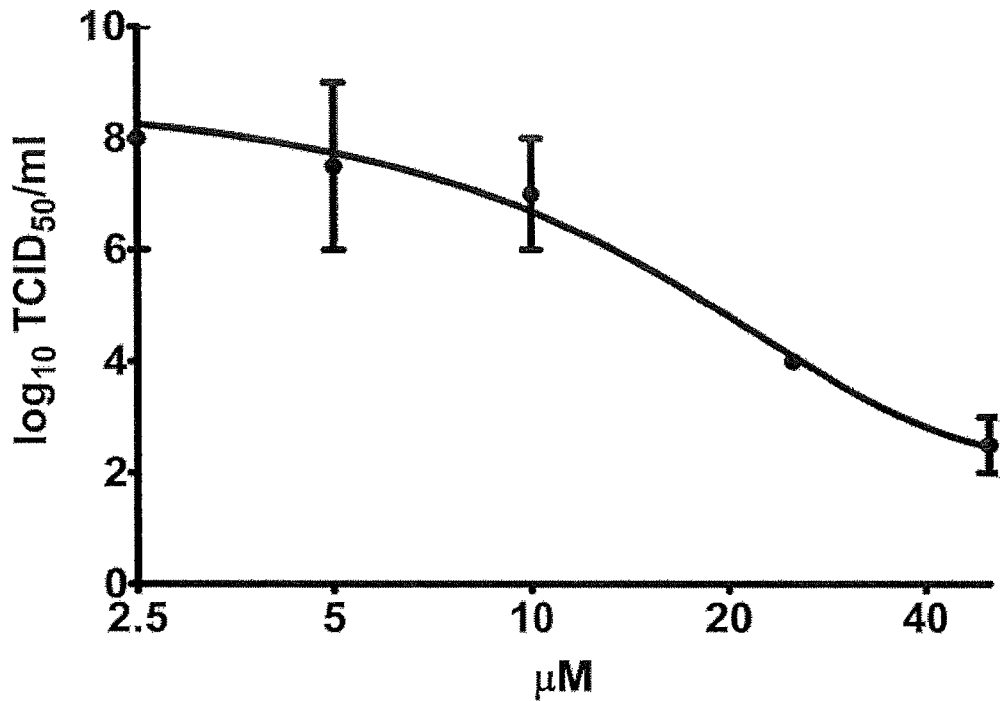
FIG. 6 shows, at different E02 concentrations, Coxsackie virus A16 in 10-fold serial dilutions were used to infect RD cells. After incubation for 2 days, CPE was observed under optical microscope and stained with crystal violet to calculate 50% tissue culture infective dose (TCID$_{50}$).

The results show 25 μM of E02 caused CVA16 titer reduction in RD cells from $1\times10^9$ $TCID_{50}$/ml to $1\times10^4$ $TCID_{50}$/ml, see FIG. 6. Therefore, E02 reduces CVA16 $TCID_{50}$ in RD cells.

Test results of the above Examples 1-3 show E02 can inhibit EV71 and CVA16 infection of RD cells in vitro. E02's $EC_{50}$ that inhibits EV71 clinical isolate is less than 6.93 μM. 10 μM of E02 can completely inhibit EV71 clinical isolate and mouse adapted strain infection of RD cells and cause CVA16 $TCID_{50}$ reduction in RD cells.

Example 4

E02 Inhibits EV71 Infection in ICR Newborn Mice

EV71 clinical isolate (EV71 FY 573) was used to infect three-day-old newborn ICR mice to test E02's efficacy to inhibit EV71 in vivo. Test mice were divided into three groups: drug group, infection group, and placebo group. When mice were two-day-old, drug group were intraperitoneally injected with 50 μl of E02 at a dose of 50 mg/kg. Infection group and placebo group were intraperitoneally injected with 50 μl of DMEM. When three-day-old, drug group was intraperitoneally injected with a mixture (50 μl) of E02 at a dose of 50 mg/kg and EV71 clinical isolate at a dose of $5\times10^7$ $TCID_{50}$. Infection group was injected with a mixture of $5\times10^7$ $TCID_{50}$ viruses (25 μl) and 25 μl of DMEM. Placebo group was injected with 50 μl of DMEM.

5 days after infection, blood was collected and serum was separated. Viral RNA in serum was extracted (viral RNA extraction kit, QIAGEN QIAamp Viral RNA Mini Kit, cat #52906). Copies of EV71 5′UTR gene and GAPDH gene were detected using one-step real-time quantitative RT-PCR kit (QIAGEN QuantiTect SYBR Green RT-PCR Kit) in ABI 7900HT 384-well plates PCR system. Reaction system and PCR program are shown in Table 3 and Table 4.

TABLE 3

EV71 5′UTR and GAPDH gene real-time
quantitative RT-PCR reaction system (SYBR)
One-step RT-PCR kit (SYBR Green)
QuantiTect SYBR Green RT-PCR Kit 204243

| Reaction system | |
|---|---|
| 2× Reaction buffer | 7.5 μl |
| Enzyme solution | 0.15 μl |
| Forward primer (5 μM) | 1.5 μl |
| Reverse primer (5 μM) | 1.5 μl |
| RNA sample | 1.5 μl |
| RNase-free water | 2.85 μl |

TABLE 4

EV71 5′UTR and GAPDH gene real-time quantitative
RT-PCR thermal cycling program (SYBR)
PCR program

| 1 | 50° C. | 30 min |
|---|---|---|
| 2 | 95° C. | 15 min |
| 3 | 94° C. | 15 sec |
| 4 | 55° C. | 30 sec |
| 5 | 72° C. | 30 sec |
| In which, repeat cycle steps 3~5 for | | |
| 40 times | | |
| Melting curve | | |

Figure 7:
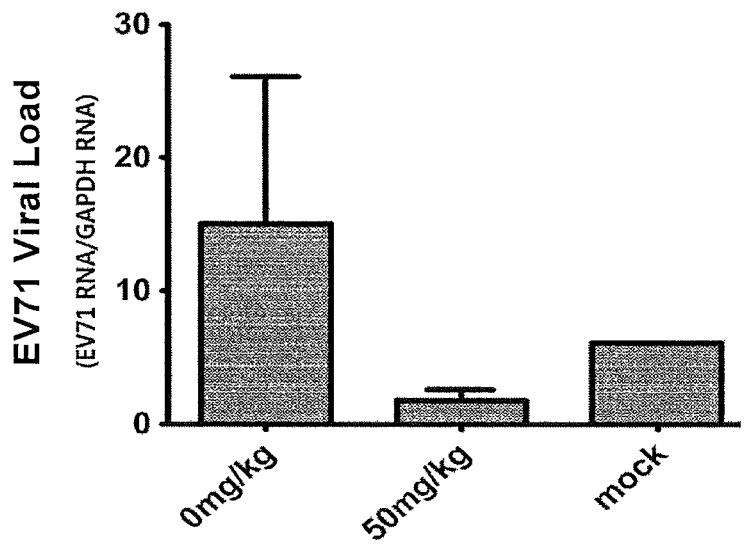
FIG. 7 shows three-day-old newborn ICR mice were infected with EV71 clinical isolates. Five days after infection, blood was collected and serum separated. Viral RNA in serum was extracted. Viral load was determined by one-step real-time quantitative RT-PCR.

RNA loading ratios between EV71 and GAPDH were calculated. Average value for the infection group is 15.0 and average value for the drug group 1.8, see FIG. 7. The results show E02 reduces EV71 viral load in mouse serum. 50 mg/kg of E02 can reduce viral load in serum of ICR newborn mice infected with EV71.

Example 5

E02 Inhibits Coxsackie Virus A16 Infection in ICR Newborn Mice

Figure 8:
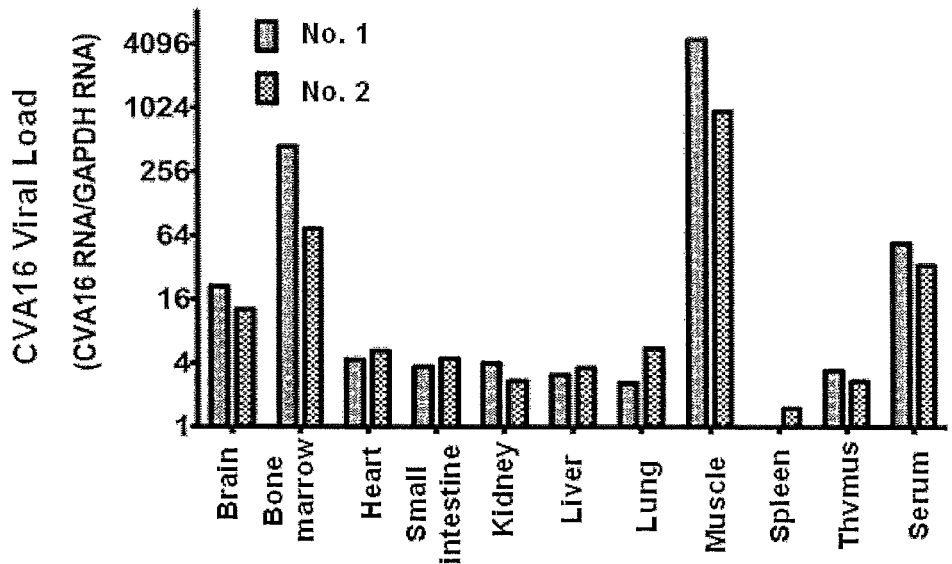
FIG. 8 shows distribution of CVA16 in various organs or tissues of ICR newborn mice. In which, No. 1 and No. 2 indicate blood samples obtained from two mice, respectively.

1. CVA16 Tissue Distribution in Mice $5 \times 10^6$ TCID$_{50}$ CVA16 viruses (50 μl) were injected to infect two three-day-old ICR newborn mice. Five days after infection, serum and tissues (brain, bone marrow, heart, intestine, kidney, liver, lung, muscle, spleen, and thymus) were collected. Viral RNA in serum was extracted (viral RNA extraction kit, QIAGEN QIAamp Viral RNA Mini Kit, cat #52906). Tissue samples were placed in RNAstore preservation solution (Tiangen, DP408-02) and stored in −80° C. refrigerator. Total tissue RNA was extracted using tissue RNA extraction kit (RNAprep pure total animal tissue RNA extraction kit). Copies of CVA16 viral genome and GAPDH gene were detected using one-step real-time quantitative RT-PCR kit (QIAGEN QuantiTect SYBR Green RT-PCR Kit) in ABI 7900HT 384-well plate PCR system. Primers are the same as that of EV71 5′UTR primers. See Table 3 and Table 4 for reaction system and PCR program. See FIG. 8 for relative viral load in each tissue and serum. Clearly, CVA16 virus was detected mainly in brain, spinal cord, muscle, and serum.

2. E02 Inhibits CVA16 Infection in ICR Newborn Mice

Three-day-old ICR newborn mice were infected with CVA16 to test E02's efficacy to inhibit EV71 in vivo. Test mice were divided into three groups: drug group, infection group, and placebo group. When mice were two-day-old, drug group were injected intraperitoneally with 50 μl of E02 at dose of 50 mg/kg. Infection group and placebo group were injected intraperitoneally with 50 μl of DMEM. When three-day-old, drug group were injected intraperitoneally with E02 at a dose of 50 mg/kg and CVA16 at a dose of $1 \times 10^4$ TCID$_{50}$ (50 μl). Infection group was injected with a mixture of CVA16 at a dose of $1 \times 10^4$ TCID$_{50}$ (25 μl) and 25 μl of DMEM. Placebo group was injected intraperitoneally with 50 μl of DMEM. 6 days after infection, tissues were obtained, blood collected, and serum separated. RNA from tissues and serum were extracted and CVA16 viral RNA determined Treatment procedures were the same as previously described in "1."

Figure 9:
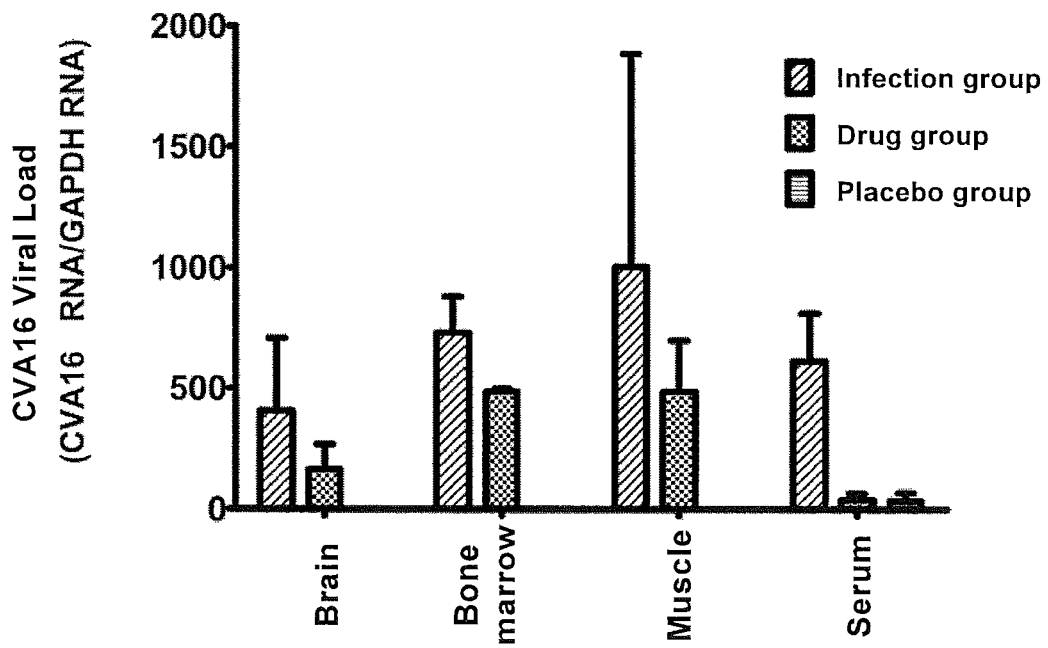
FIG. 9 shows three-day-old newborn ICR mice were infected with CVA16. Six days after infection, tissues were obtained, blood collected, and serum separated. RNA from tissues and serum were extracted. CVA16 RNA was measured to calculate viral load.

See FIG. 9 for the results. The results show 50 mg/kg of E02 significantly decreased CVA16 RNA in brain, bone marrow, muscle, and serum of ICR newborn mice.

To summarize Example 4-5, tests in ICR newborn mice show 50 mg/kg of E02 can inhibit EV71 and Coxsackie virus A16 in vivo.

Example 6

E02 Safety, Tolerability, and Toxicity Tests

1. E02 has No Cytotoxicity In Vitro

Figure 10:
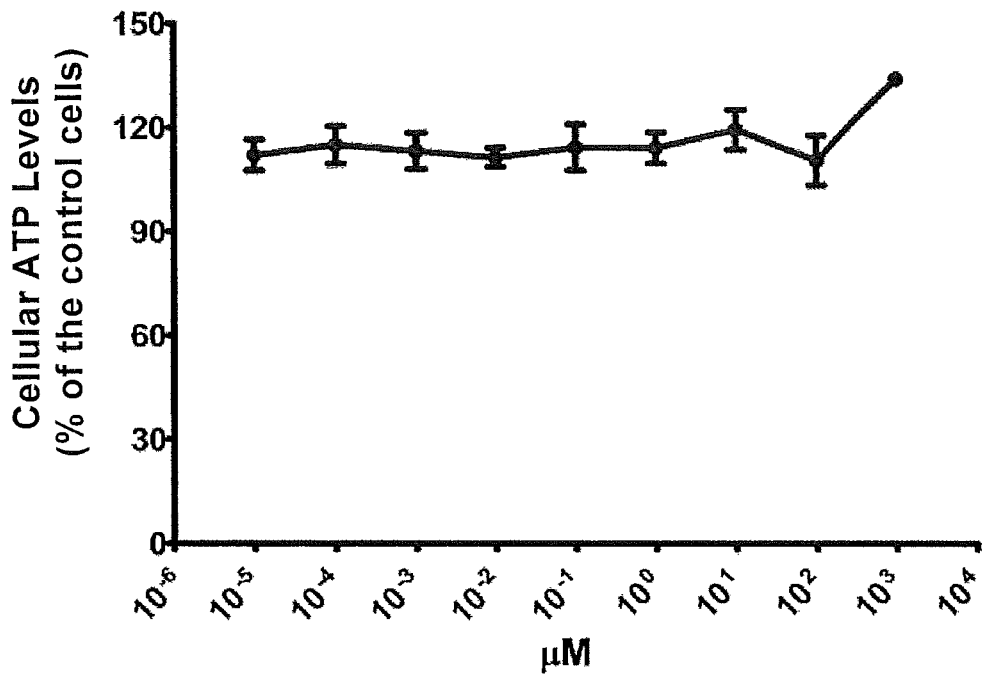
FIG. 10 shows cytotoxicity of RD cells at different E02 concentrations determined by using Celltiter Glo reagents.

Cytotoxicity to RD cells at different E02 concentrations was measured using Celltitr Glo reagents as follows:
(1) Cells seeding: 24 h prior to testing, RD cells were seeded in 96-well cell culture plates at $5 \times 10^4$ per well;
(2) Cells incubated with E02: medium was removed from cell culture plates, 180 μl of DMEM containing 2% FBS was added, and then added 20 μl of DMEM solution with corresponding concentration of E02, placed in 37° C., 5% $CO_2$ incubator for incubation;
(3) After cultured for 46 h, cellular ATP levels were measured using the PROMEGA Celltitr Glo reagents according to reagent instructions.
Testing results show $1 \times 10^{-6}$ to $1 \times 10^4$ μM of E02 had no cytotoxicity to RD cells, see FIG. 10.

2. E02 is Non-Toxic to ICR Newborn Mice

Figure 11:
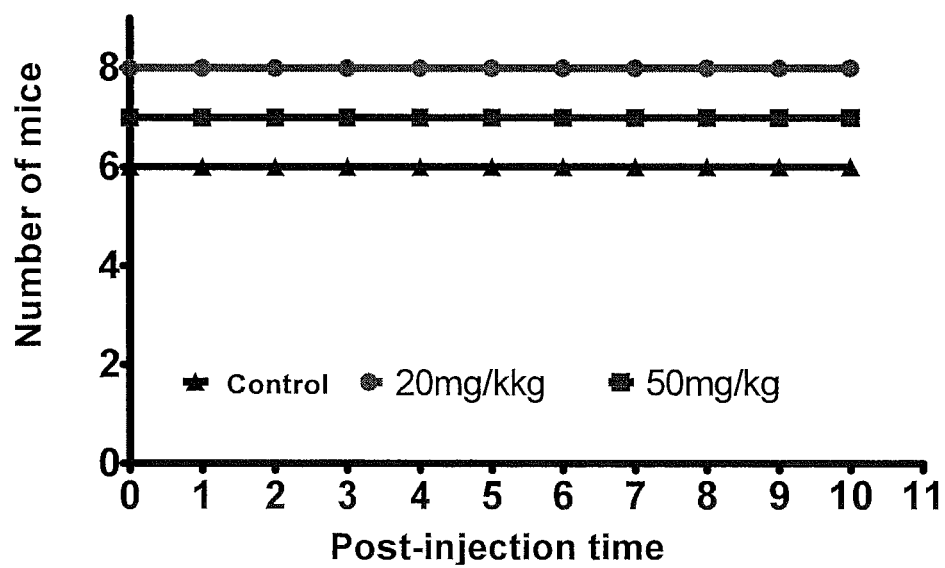
FIG. 11 shows three-day-old ICR mice were injected intraperitoneally and daily with a dose of 50 µl of 50 mg/kg E02, 20 mg/kg E02, or 50 µl of DMEM for 4 consecutive days. Toxicity results were observed.

Three-day-old ICR mice were injected intraperitoneally and daily with 50 μl of E02 at a dose of 50 mg/kg, 20 mg/kg, or 50 μl of DMEM for 4 consecutive days. No toxicity was observed, as shown in FIG. 11.

Example 7

E02 Inhibits EV71 Clinical Isolates SH-TS and SH-RS Infection of RD Cells

1. E02 Inhibits the Replication of EV71 SH-TS and SH-RS in RD Cells

RD cells were infected with EV71 SH-TS or SH-RS at different E02 concentrations, at the MOI of 0.1. After cultured for 46 h, viral RNA in culture supernatant was extracted. Relative EV71 viral load was determined by quantitative RT-PCR. See Example 1 for specific procedures of quantitative RT-PCR.

Figure 15:
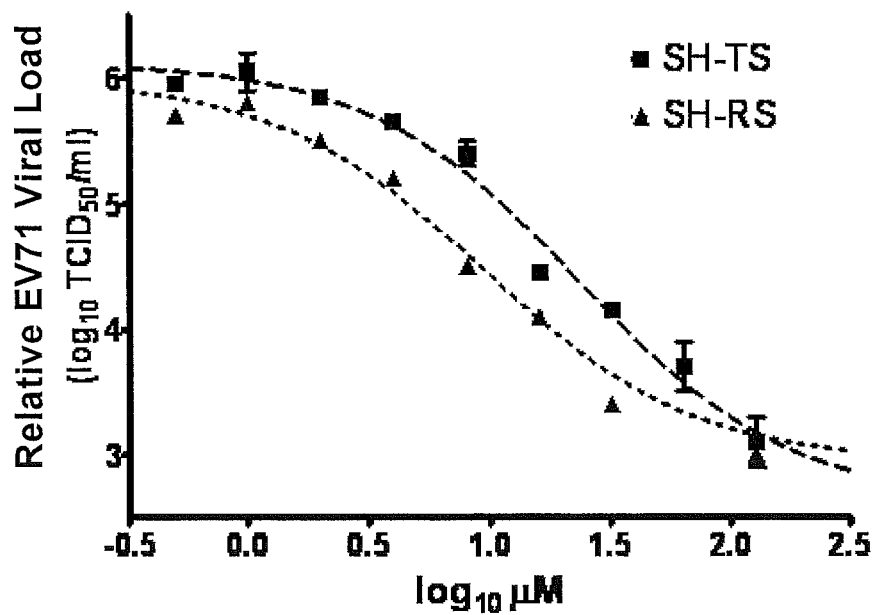
FIG. 15 shows E02 inhibits the replication of EV71 isolates SH-TS and SH-RS in RD cells.

The results show E02 can inhibit the replication of EV71 clinical isolates SH-TS SH-RS in RD cells. For SH-TS, 7.14 μM can reduce EV71 replication by 10-fold and 25.35 μM can reduce EV71 replication by 100-fold. For SH-RS, 4.41

μM can reduce EV71 replication by 10-fold and 16.29 μM can reduce EV71 replication by 1000-fold, as shown in FIG. 15.

Therefore, E02 inhibits the replication of EV71 SH-TS and SH-RS in RD cells.

2. E02 inhibits EV71 SH-TS and SH-RS infection of RD cells (plaque forming units, PFU)

RD cells cultured in 12-well plates were infected with EV71 SH-TS or SH-RS at different E02 concentrations. After cultured for 5~7 days, cells were stained and plaque-forming units were calculated. Same procedure is as detailed in "3. E02 reduces EV71 plaque forming units in RD cells" of Example 1.

Figure 16:
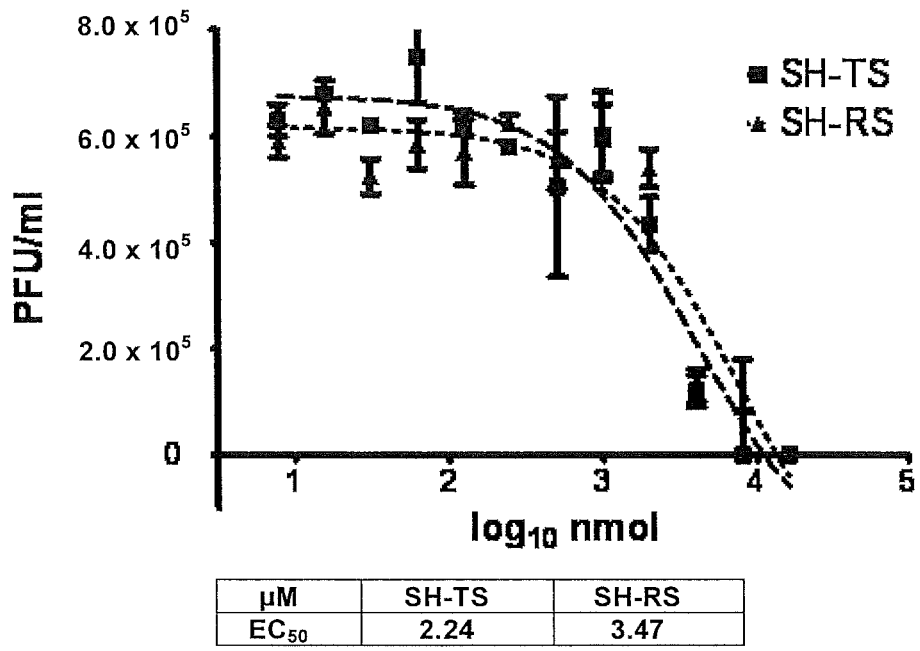
FIG. 16 shows E02 reduces PFU of EV71 isolates SH-TS, SH-RS in RD cells.

The results, $EC_{50}$ of E02 to reduce EV71 SH-TS PFU in RD cells is 2.24 μM, for SH-RS, 3.47 μM, as shown in FIG. 16.

Viral replication and PFU tests show E02 can inhibit EV71 clinical isolates SH-TS and SH-RS infection of RD cells.

Example 8

E02 Inhibits Cambodia EV71 Isolate SEP-4 Infection of Vero Cells

Vero cells were infected with EV71 SEP-4 virus strain (provided by Institut Pasteur of Cambodia, Cambodia strain) at different E02 concentrations, at the MOI of 0.1. After cultured for 46 h, viral RNA in culture supernatant was extracted. Relative EV71 viral load was determined by quantitative RT-PCR. For specific procedures, refer to Example 1.

Figure 17:
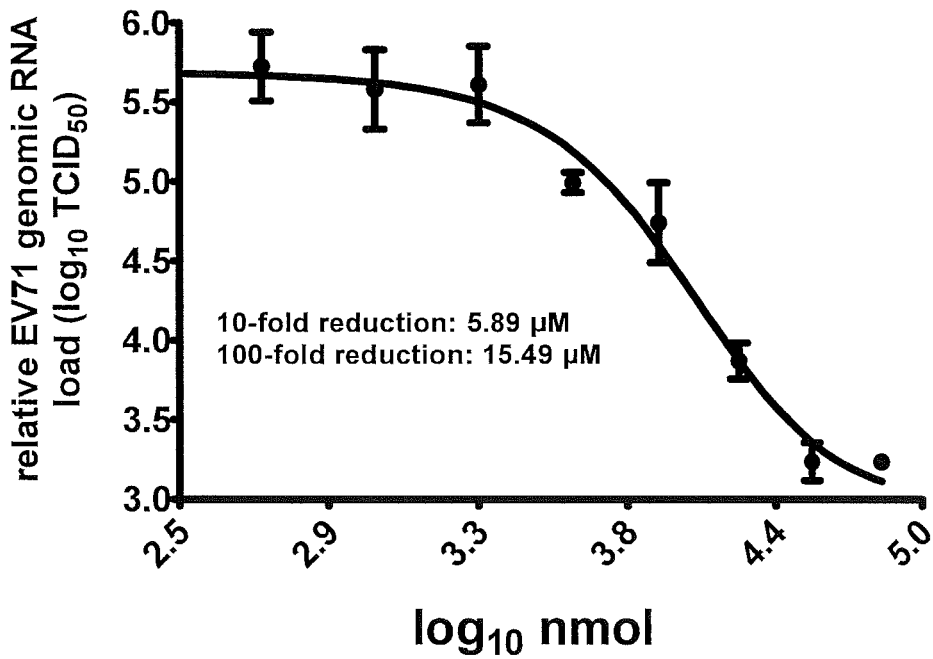
FIG. 17 shows E02 inhibits the replication of EV71 isolate SEP-4 in Vero cells.

The results show E02 can inhibit EV71 SEP-4 replication in Vero cells. 5.89 μM of E02 can reduce EV71 replication by 10-fold and 15.49 μM reduced EV71 replication by 100-fold, as shown in FIG. 17.

Example 9

E02 Inhibits EV71 Replication in Rhesus Monkey 10 adult rhesus monkeys, which were detected negative for EV71 antibody (rhesus monkey (*Macaca*), Source: Institute of Medical Biology, Chinese Academy of Medical Sciences, Experimental animal use license number: SYXK (Yunnan) 2010-0009, Certification unit: Yunnan Provincial Science and Technology Agency), were randomly divided into two groups, namely: five in control group (aged about 4 years old, weighing about 5.3 kg, injected with physiological saline), 5 in treatment group (aged about 4.6 years old, weighs about 5.44 kg, injected with 50 mg/kg suramin). Multiple intravenous injections of suramin (50 mg/kg) were used. One day after the initial injection of suramin, infected with 4.5 $lgCCID_{50}$EV71 FY-23 (EV71-FY23 strain (provided by Chinese Academy of Medical Sciences, Institute of Medical Biology, Virus Immunology laboratory), batch number: 20121001, content: 7.5 $lgCCID_{50}$/ml, storage conditions: −80° C.), viral load was determined daily in infected adult rhesus monkeys (>3 years old), clinical symptoms and body temperature were observed to analyze the effect of the drug on treating and preventing EV71 infection. Specific experimental procedure is as follows:

1) One day prior to infection: background whole blood and serum were collected, body temperature measured, animals' appearance, behavior, mental state, and local drug administration were observed for abnormality, etc. Then, drug was administered intravenously at a dose (50 mg/kg suramin or physiological saline).

2) On the day of infection (Day 0): body temperature measured, animals' appearance, behavior, mental state, and local drug administration were observed for abnormality, etc. Intravenous viral challenge was performed with 4.5 $lgCCID_{50}$ EV71 FY-23.

3) During infection period (1-14 days): body temperature was measured daily, animals' appearance, behavior, mental state, and local drug administration were observed for abnormality, etc., and viral load determined Intravenous administration at a dose (50 mg/kg suramin or physiological saline) on day 1, 3, 5 after infection.

4) Late stage of infection (21 and 28 days), body temperature was measured, animals' appearance, behavior, mental state, and local drug administration were observed for abnormality, etc., and viral load determined.

Blood Viral Load Testing

Whole blood RNA extraction: obtained 0.2 ml blood, added 0.8 ml TRNzol-A$^+$, after mixing, placed the well at room temperature for 10 min; added 0.2 ml chloroform, tightened cover lid, vigorously shaking for 15 sec, placed at room temperature for 5 min, centrifuged at 12500 rpm, 4° C., 20 min, 0.4 ml of aqueous phase was transferred to another fresh tube, equal volume of isopropanol was added, mixed, placed at room temperature for 30 min; centrifuged at 12500 rpm, 4° C., 20 min, supernatant was discarded, 1 ml of 75% ethanol was added to wash precipitates, centrifuged at 12500 rpm, 4° C., 30 min. Supernatant discarded, placed at room temperature for 30 min, RNA dried, 20 μl RNase-free ddH$_2$O added, and RNA fully dissolved. Viral load was determined by measurement method as follows:

1) Standard dilutions: obtaining standards (performed according to TaKaRa MiniBEST Viral RNA/DNA extraction Kit Ver 3.0 instructions), 10 μl standards were obtained, 10-fold serial dilutions $10^6$, $10^5$, $10^4$, $10^3$, $10^2$, $10^1$, $10^0$.

2) Primer sequences (Taqman probe method):

Upstream primer (10 μM):
5'-agcccaaaagaacttcacta-3';

Downstream primer (10 μM):
5'-atccagtcgatggctgctca-3';

Probe 5-FAM-agtgatatcctgcagacgggcaccatcc-TAMRA-3.

3) Preparing RT-PCR reaction solution (reaction solutions were prepared on ice):
2× One Step RT-PCR Buffer III: 10 μl
TaKaRa Ex Taq™ HS (5 U/μl): 0.4 μl
Primescript™ RT Enzyme Mix II: 0.4 μl
Upstream primer (10 μM): 0.4 μl
Downstream primer (10 μM): 0.4 μl
Probe: 0.8 μl
ROX Reference Dye II: 0.4 μl
Total RNA: 2 μl
RNase Free dH$_2$O: 5.2 μl
Total: 20 μl 4) Performing Real Time One Step RT-PCR.

1. Viral Load Testing 10 test animals were challenged with 4.5 $lgCCID_{50}$ of EV71 FY23. Animals in control group exhibited a transient increase of viral load (reaching $1$-$1.5 \times 10^3$ copies/ml) in the $6^{th}$ and $7^{th}$ days after viral challenge and began to decline after the $8^{th}$ day. In the $9^{th}$ day after viral challenge, they exhibited a transient increase of viral load (reaching $5.25 \times 10^2$ copies/ml) and began to decline after the $10^{th}$ day.

Figure 18:
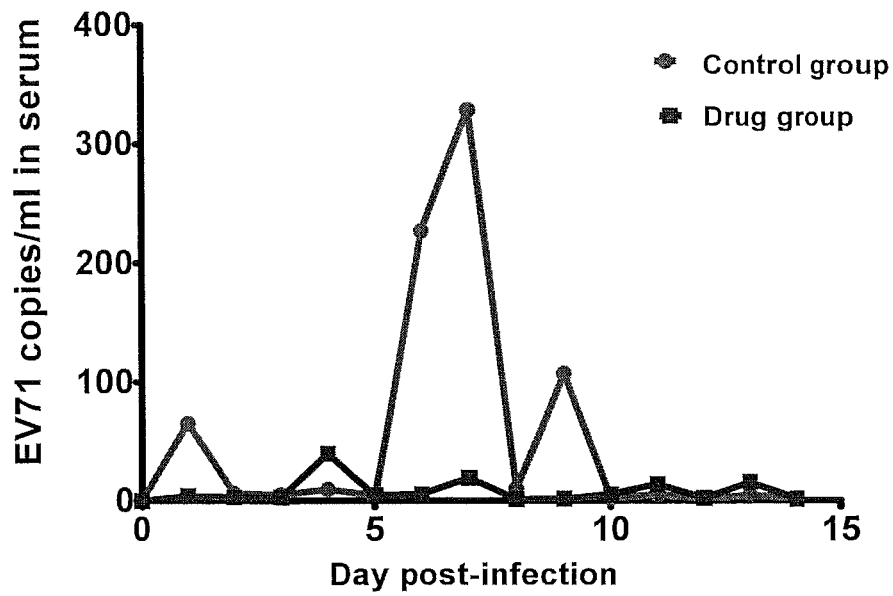
FIG. 18 shows E02 inhibits the replication of EV71 in rhesus monkeys in vivo.

Animals in drug treatment group exhibited, respectively, slightly elevated viral load (average $1.5\times10^1$ copies/ml) in the $4^{th}$, $7^{th}$, and $13^{th}$ days after viral challenge. Viral loads were significantly lower than that in control group, as shown in FIG. 18.

2. Body Temperature Measurement

Figure 19:
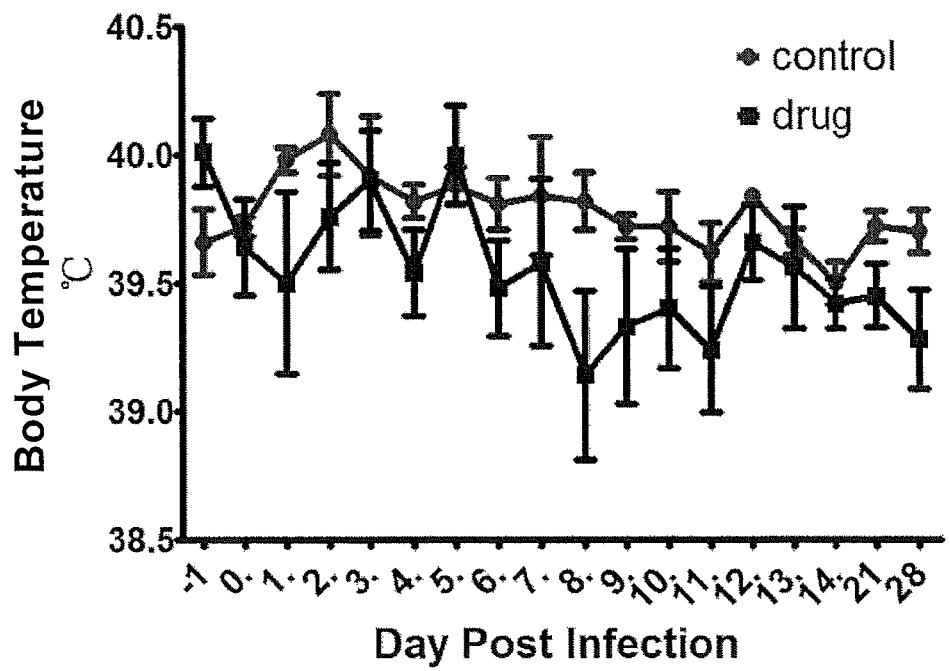
FIG. 19 shows E02 inhibits body temperature rise caused by EV71 in rhesus monkey.

Animals in control group show certain rise in body temperatures 1 day after infection and subsequently (about 3 days after infection) reduced to within normal range. Animals in drug treatment group essentially maintained body temperatures within normal range, as shown in FIG. 19.

Conclusions: Under the present experimental conditions, after intravenous infection of 4.5 lgCCID50 EV71, adult rhesus monkeys of control group exhibited certain increase in viral loads within specific time periods and also a slight rise in body temperatures. In contrast, adult rhesus monkeys of drug treatment group exhibited, within that specific time period, slightly elevated viral load, which was significantly lower than that of the control group, and body temperature measurements did not show significant changes.

Example 10

Identification of E02 Targets

1. E02 Inhibits EV71 Entry into Cells

RD cells in 96-well plates were infected with MOI 10 EV71 clinical isolate EV71 FY573. In three periods at prior to, during, and post infection, 32 μM of E02 (dissolved in DMEM) or DMEM were added, EV71 replication was measured to determine the stage, in which E02 inhibits EV71 infection. Steps are detailed as follows:

(1) Cell seeding: 24 h prior to infection, RD cells were seeded in 96-well cell culture plates, $5\times10^4$ cells per well;

(2) Cells pre-incubated with drug: cell culture medium was removed from 96-well plates, each well was added 100 μl of DMEM, and then added 11 μl of 320 μM E02 solution (cell group treated with drug) or 11 μl of DMEM (cell group without drug treatment), incubated at 37° C. for 1 h.

(3) Virus pre-incubated with drug: virus stock solution was diluted to $5\times10^6$ $TCID_{50}$/ml with DMEM, dispensed to 96-well plates at 100 μl per well, and 11 μl of 320 μM E02 solution (B and C groups) or 11 μl of DMEM (A and F groups) were added, and incubated at 37° C. for 1 h.

(4) Infection: After cells and virus were incubated for one hour, drug was discarded from cell culture plates. 111 μl of pre-incubated virus with drug (B and C groups) or DMEM (A and F groups) was transferred to cell culture plates. After 100 μl of virus solution was transferred to D and E groups, 11 μl of 320 μM E02 was added, and incubated at 37° C. for 1 h.

(5) One hour after viral infection of cells, virus and drug mixture was discarded from cell culture plates. Cells were washed twice with 50 μl of DMEM. 180 μl per well of DMEM containing 2% FBS, 20 μl of 320 μM E02 solution (B, E, and F groups) or 20 μl of DMEM (A, C, and D groups) were added. Cell culture plates were placed in 37° C., 5% carbon dioxide incubator for incubation.

(6) Virus harvesting and RNA extraction: at 18 h post infection, 140 μl of supernatant was transferred to 96-deep well plates, viral RNA extraction was performed using viral RNA extraction kit (QIAGEN QIAamp Viral RNA Mini Kit, cat #52906) according to the kit standard operating procedures.

(7) Viral load determination: EV71 5'UTR gene was detected using ABI Taqman one-step RT-PCR kit (ABI taqMan® One-Step RT-PCR, Cat #4309169) in ABI 7900HT 384-well plates PCR system. See Table 1 and Table 2 for reaction system and PCR program.

(8) PCR standard curves were used to convert CT values of PCR to viral load (standard curves were obtained by CT values determined by performing RT-PCR on RNA extracted from viruses with defined titers at 10-fold serial dilutions).

Figure 12:
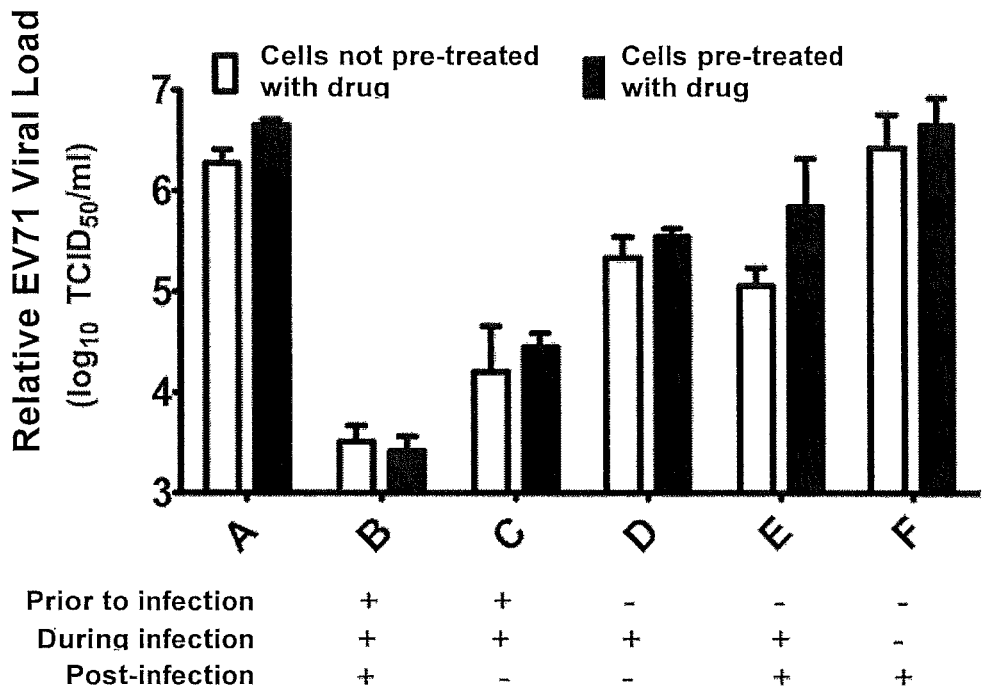
FIG. 12 shows testing of time of E02 addition assay. Potency of E02 to inhibit EV71 infection was tested by adding E02 prior to infection (B, C), during infection (D, E), and after infection (F), respectively.

Infecting cells with high MOI caused most cells to be infected synchronously. 18 hours of incubation ensured virus only amplified once. The infection conditions may determine which stage of virus life cycle plays a role in drug-induced viral inhibition (Bonavia, Franti et al., 2011; Daelemans, Pauwels et al., 2011). As shown in FIG. 12, test results of time of E02 addition assay showed addition of E02 prior to infection (B, C) and during infection (D, E) can inhibit EV71 infection, whereas E02 added after infection (F), could not inhibit EV71 infection. If drug has been added during infection, whether or not drug added after infection (D and E) had no significant effect on viral replication. The results show E02 inhibits EV71 infection by inhibiting EV71 entry into cells.

2. P2X Receptor Antagonists can Inhibit EV71 Infection

E02 is antagonist to the sensing receptor P2X and can inhibit P2X1, 2, 3, and 5 subtype receptors (Khakh, Burnstock et al., 2001; Burnstock, 2004; Coddou, Yan et al., 2011), i.e., an antagonist of P2X1, 2, 3, and 5 subtype receptors. P2X is a member of ATP-gated ion channel family of proteins, expressed on cell membrane, usually homologous or heterologous trimer, formed by an extracellular domain, two transmembrane domains and two intracellular domains. P2X family includes seven subtypes. Triggered by extracellular ATP, P2X ion channels open, causing calcium influx, intracellular calcium accumulation. A series of downstream signal transduction is activated through MAPK, PKC and calmodulin (Erb, Liao et al., 2006). P2X receptors are widely distributed in higher animal tissues (Valera, Hussy et al., 1994), expressed in various parts of CNS, and play a role in transduction of neuronal synapses triggered sensing signals (such as pain, taste, hearing, etc.), smooth muscle contraction, blood pressure control in cardiovascular system, and inflammatory response (Surprenant and North, 2009).

EV71 infection of central nervous system can cause acute flaccid paralysis, acute spread myelitis, and acute transverse myelitis, and also can cause aseptic meningitis and encephalitis. Enterovirus infection may also cause potential behavior and memory impairment (Yang, Wang et al., 2009; Rhoades, Tabor-Godwin, et al. 2011). EV71 leads to mainly neurological disorders through inducing CNS inflammation in patents with viral infection. EV71 infection can cause inflammation at all levels of cerebral cortex, brainstem, and spinal cord. EV71-infected patients often die of pulmonary edema or hemorrhage. Studies showed that EV71 pulmonary edema is neurological (Solomon, Lewthwaite et al., 2010). Among EV71-infected patients, who died of pulmonary syndrome, inflammation was detected only in spinal cord and brain, whereas viral particles and inflammation were undetectable in lungs and heart. (Weng, Chen et al., 2010). Linking disease characteristics caused by EV71 infection with the distribution and physiological role of P2X, the present inventors believe that P2X plays an important role in EV71 pathology.

Accordingly, in this embodiment, the present inventors used chemical probes (known P2X antagonists or agonists) to determine the role of P2X receptors in EV71 infection.

1. PPADS Inhibits EV71 Infection of RD Cells

PPADS is an E02 analog (Khakh, Burnstock et al., 2001; Burnstock 2004; Coddou, Yan et al. 2011) and has a similar inhibitory effect on P2X subtypes to that of E02. RD cells were infected with EV71 clinical isolate FY 573 at different PPADS concentrations to determine the inhibitory effect of PPADS on EV71 replication. Detailed procedure is the same as that in "1" of Example 1. In addition, cytotoxicity to RD cells at each concentration of PPADS was determined. Detailed procedure is the same as that in "1" of Example 6.

Figure 13:
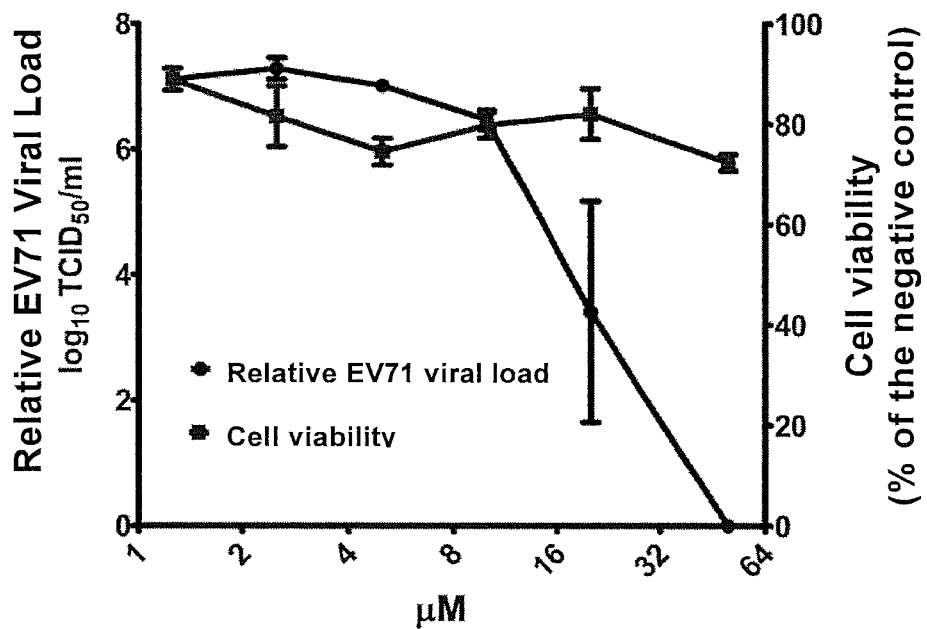
FIG. 13 shows, at different PPADS concentrations, EV71 clinical isolates were used to infect RD cells. Inhibitory potency of PPADS on EV71 replication was determined.

The results are shown in FIG. 13, PPADS concentrations lower than 64 μM are not cytotoxic to RD cells. $EC_{50}$ for inhibiting EV71 replication is 18.9 μM.

2. P2X Receptor Expression in RD Cells

Total RNA was extracted from RD cells. Each P2X subtype mRNA was amplified by one-step RT-PCR. PCR product length was determined by gel electrophoresis. Specific procedures are as follows:

① Total cellular RNA extraction: $2\times10^6$ RD cells were obtained and total RNA extracted using QIAGEN RNeasy kit. Experiments were performed according to kit instructions. Products were dissolved in 50 μl of nuclease-free water.

② PCR: each P2X subtype and GAPDH mRNA was amplified by one-step RT-PCR. Reaction system and cycling program are as shown in Table 5 and Table 6.

③ Electrophoresis: PCR product size was detected by 2% gel electrophoresis.

TABLE 5

P2X mRNA RT-PCR reaction system
One-step RT-PCR kit
qiangen 201202

| Reaction system | 25 μl |
|---|---|
| 5× reaction buffer | 5 μl |
| Enzyme solution | 1 μl |
| Forward primer (10 μM) | 1.5 μl |
| Reverse primer (10 μM) | 1.5 μl |
| dNTP | 1 μl |
| RNA sample | 2 μl |
| RNase-free water | 14 μl |

TABLE 6

P2X mRNA RT-PCR thermal
cycling program PCR program

| 1 | 50° C. | 30 | min |
|---|---|---|---|
| 2 | 95° C. | 15 | min |
| 3 | 94° C. | 15 | sec |
| 4 | 50° C. | 60 | sec |
| 5 | 72° C. | 60 | sec |

Cycling steps 3~5 for 40 times
72° C. for 10 min

Figure 14:
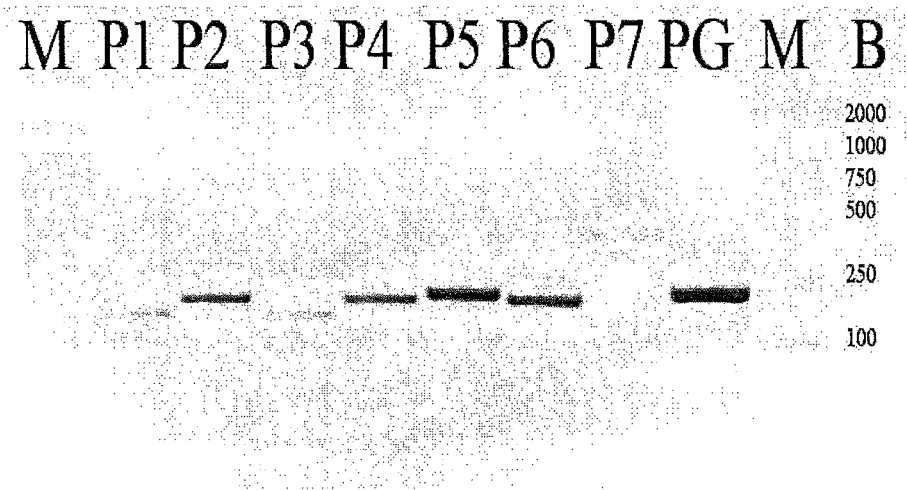
FIG. 14 shows mRNA expression level of six P2X subtypes in RD cells was determined by RT-PCR method.

Electrophoresis results show, except for P2X7, the other six P2X subtype receptors are expressed in RD cells. Results are shown in FIG. 14.

3. P2X Receptor Antagonists Inhibit EV71 Infection of RD Cells

Inhibitory effect of each P2X receptor antagonists and agonists on EV71 replication was measured at 0.1, 1, 10, and 100 μM. Specific procedures refer to "1" of Example 1. after infection, however, cells need to be incubated for 3~4 days, stained with crystal violet, and observed under optical microscope to determine whether or not CPE (cytopathic effect) was present. In addition, the effect of compounds at each concentration on cytotoxicity to RD cells was determined. After culturing RD cells in various concentrations of compounds for 3~4 days, stained with crystal violet, and observed under optical microscope to observe whether or not cell layer was damaged. Compounds capable of protecting cells from infection without damage of healthy cell layer can inhibit EV71 replication in RD cells.

Figure 20A:
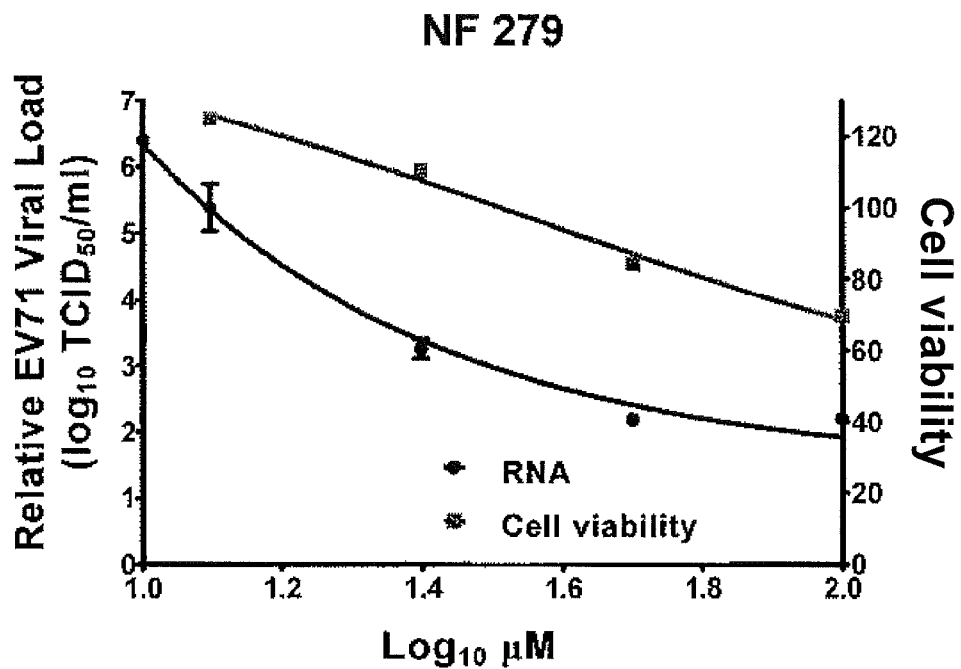
FIGS. 20A-F show various P2X receptor antagonists inhibit EV71 replication in RD cells.
Figure 20B:
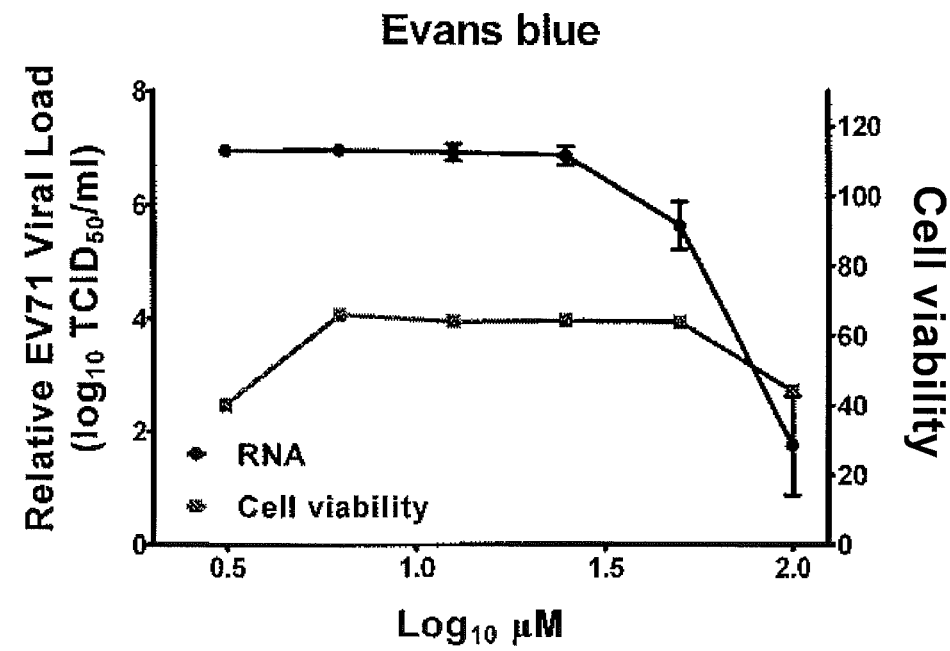
Figure 20C:
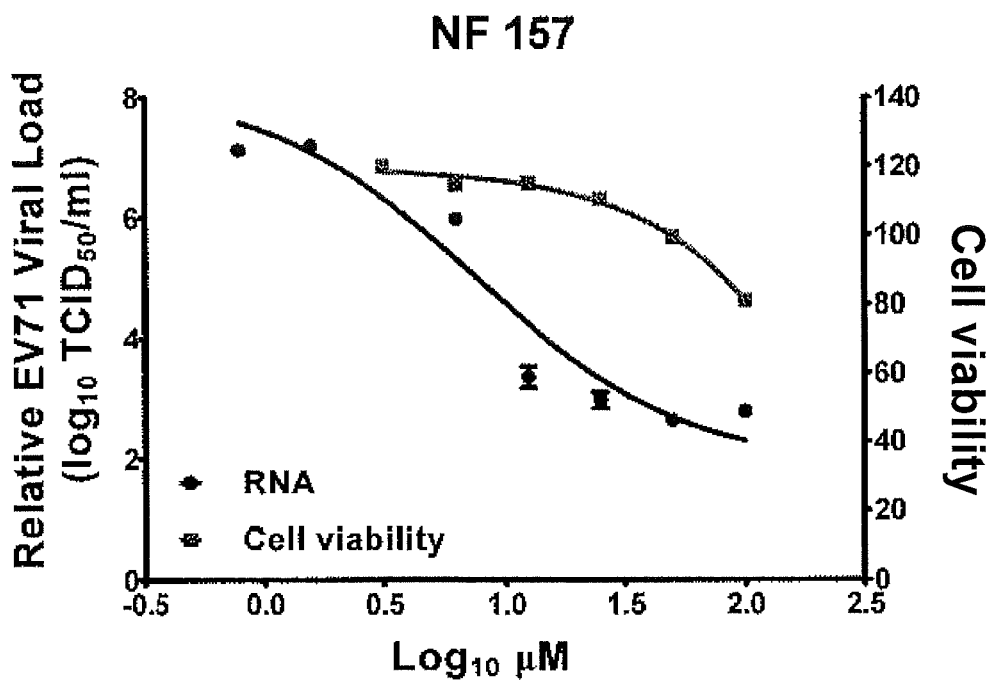
Figure 20D:
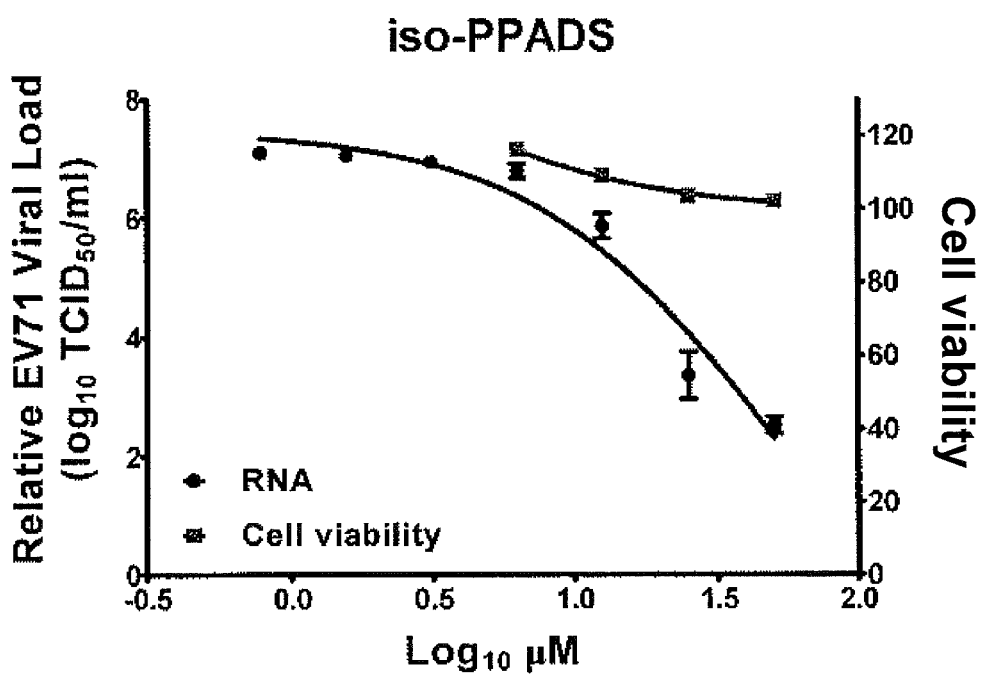
Figure 20E:
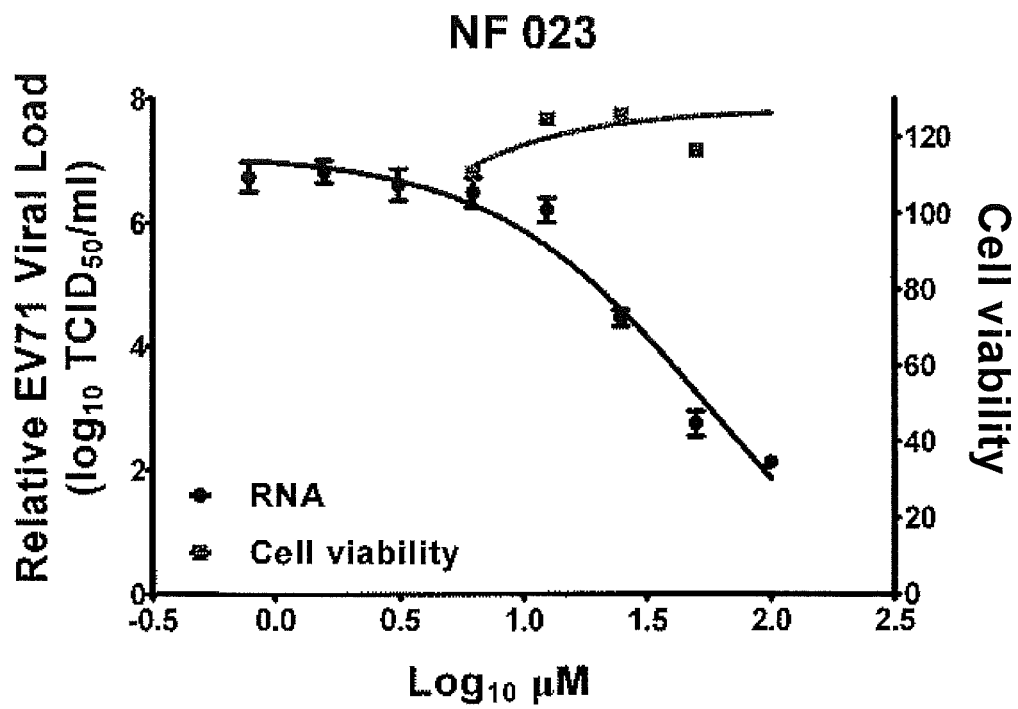
Figure 20F:
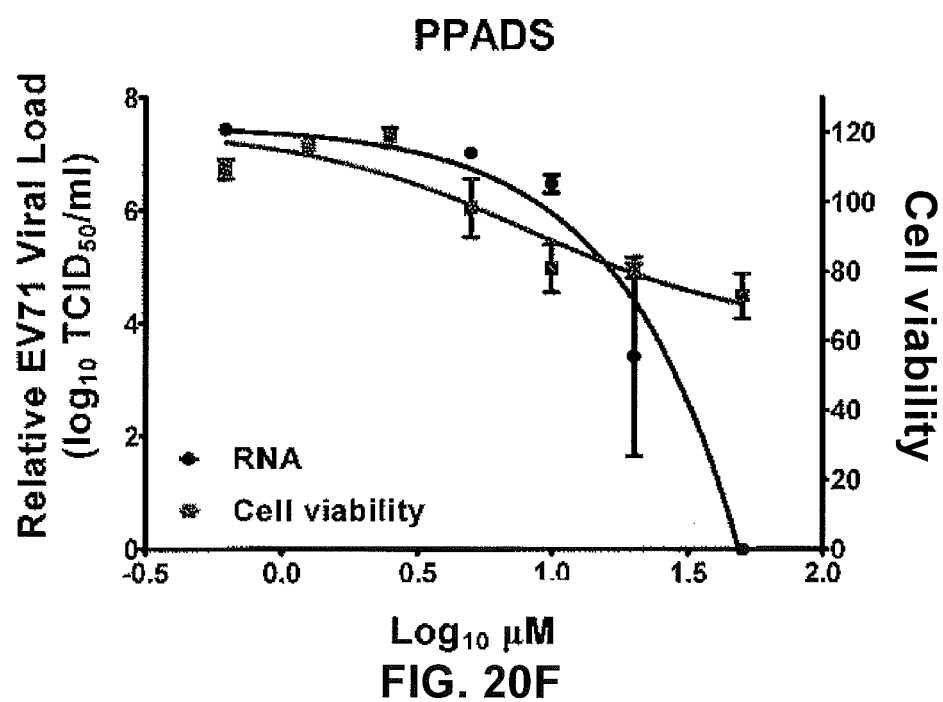

The results are shown in Table 7 and FIGS. 20A-F. FIG. 20A shows inhibition by NF279. FIG. 20B shows inhibition by Evans Blue. FIG. 20C shows inhibition by NF157. FIG. 20D shows inhibition by iso-PPDAS. FIG. 20E shows inhibition by NF023. FIG. 20F shows inhibition by PPADS. Other than E02 and PPADS, P2X receptor antagonists iso-PPADS, NF023, NF279, NF157, TNP-ATP, PPNDS, and Evans Blue can also inhibit EV71 replication.

TABLE 7

P2X receptor antagonists inhibit EV71 replication in RD cells

| | | Inhibition of EV71 replication | | | |
|---|---|---|---|---|---|
| | Compounds | 100 μM | 10 μM | 1 μM | 0.1 μM |
| Antagonists | E02 | + | + | − | − |
| | PPADS | + | + | − | − |
| | iso-PPADS | + | − | − | − |
| | NF023 | + | + | − | − |
| | NF279 | + | + | − | − |
| | NF157 | + | + | − | − |
| | TNP-ATP | + | − | − | − |
| | PPNDS | + | + | − | − |
| | Evans Blue | + | − | − | − |
| Agonists | Ivermectine | − | − | − | − |
| | bzATP | − | − | − | − |
| | UTP | − | − | − | − |

Comparison between the inhibitory effect of these compounds on P2X and EV71 infection, as shown in Table 8, indicates P2X receptors play an important role in EV71 infection of RD cells.

TABLE 8

| | | P2X receptors | | | | | | | Inhibition of EV71 replication |
|---|---|---|---|---|---|---|---|---|---|
| | | 1 | 2 | 3 | 4 | 5 | 6 | 7 | 2/3 | |
| Agonists | Bz-ATP (Burnstock 2004) | +++ | ++ | + | +++ | ++ | | ++ | | − |
| | UTP (Burnstock 2004) | − | − | − | − | + | | | | − |
| | Ivermectin (Khakh, Proctor et al. 1999) | | | | ++ | | | | | − |
| Antagonists | PPADS (Burnstock 2004) | ++ | ++ | ++ | − | ++ | + | + | | + |
| | Iso-PPADS (Burnstock 2004) | ++ | ++ | ++ | | | | | | + |
| | NF023 (Burnstock 2004) | ++ | + | + | | | | | | + |
| | NF279 (Burnstock 2004) | +++ | + | + | − | | | + | | + |
| | TNP-ATP (Burnstock 2004) | +++ | + | +++ | + | + | | + | | + |
| | PPNDS (Burnstock 2004) | ++ | | | | | | | | ++ |
| | E02 (Burnstock 2004) | ++ | + | + | − | ++ | − | − | | + |

Notes:

Agonists: −: no activity, +: activating concentration >10 μM, ++: activating concentration 1~10 μM, +++: activating concentration <1 μM;

Antagonists: −: no activity, +: inhibitory concentration >300 nM, ++: inhibitory concentration = 10~300 nM, +++: inhibitory concentration <10 nM.

Figure 21A:
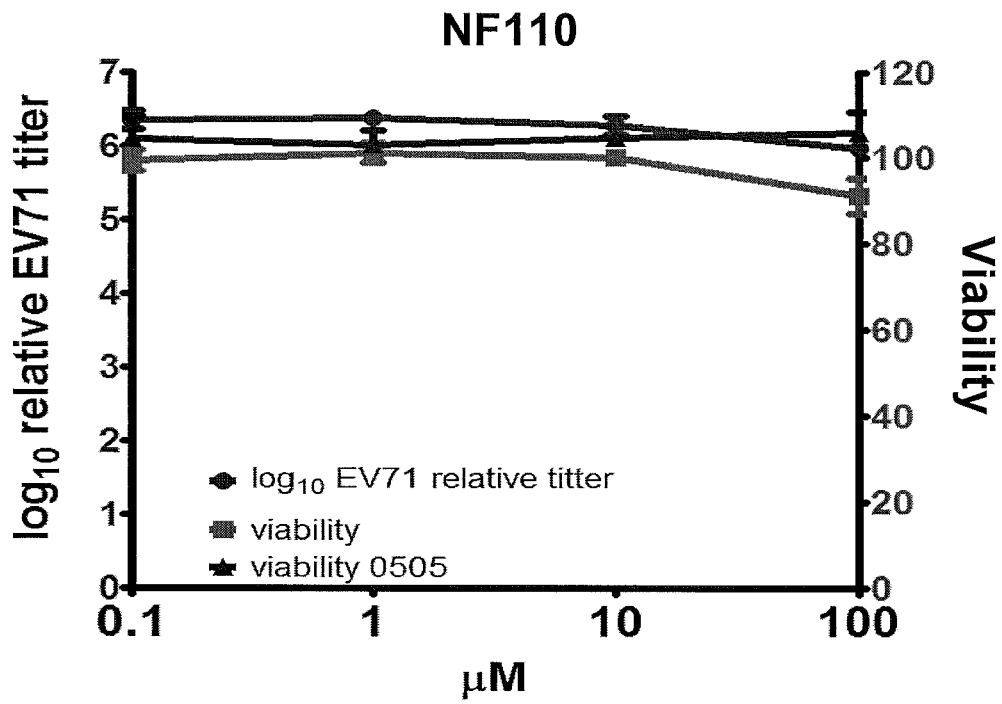
FIGS. 21A-X show effects of other antagonists and agonists on EV71.
Figure 21B:
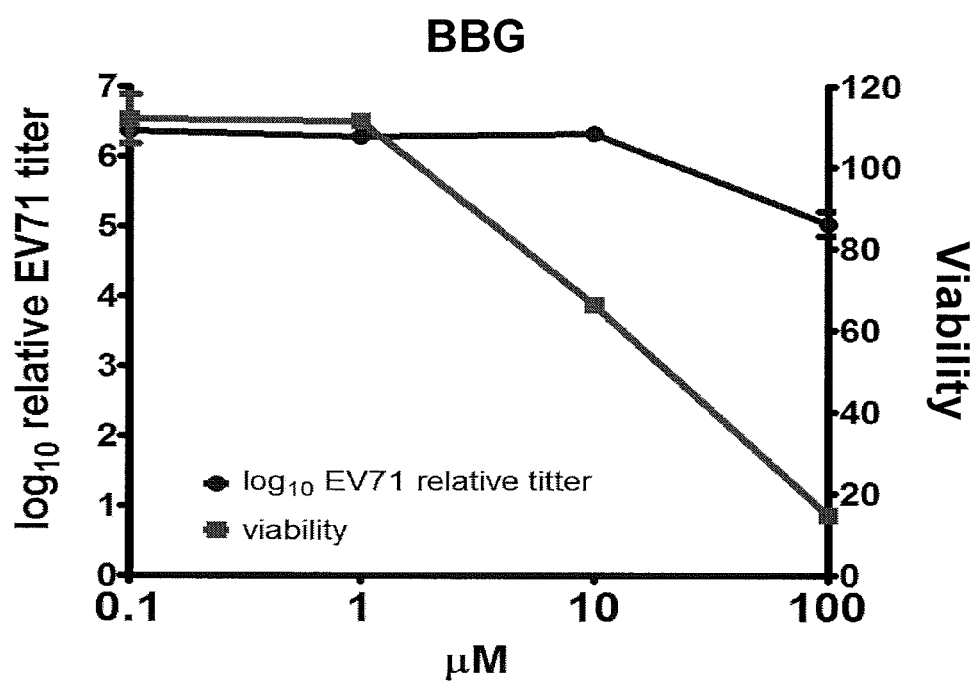
FIG. 21B shows inhibition by BBG.
Figure 21C:
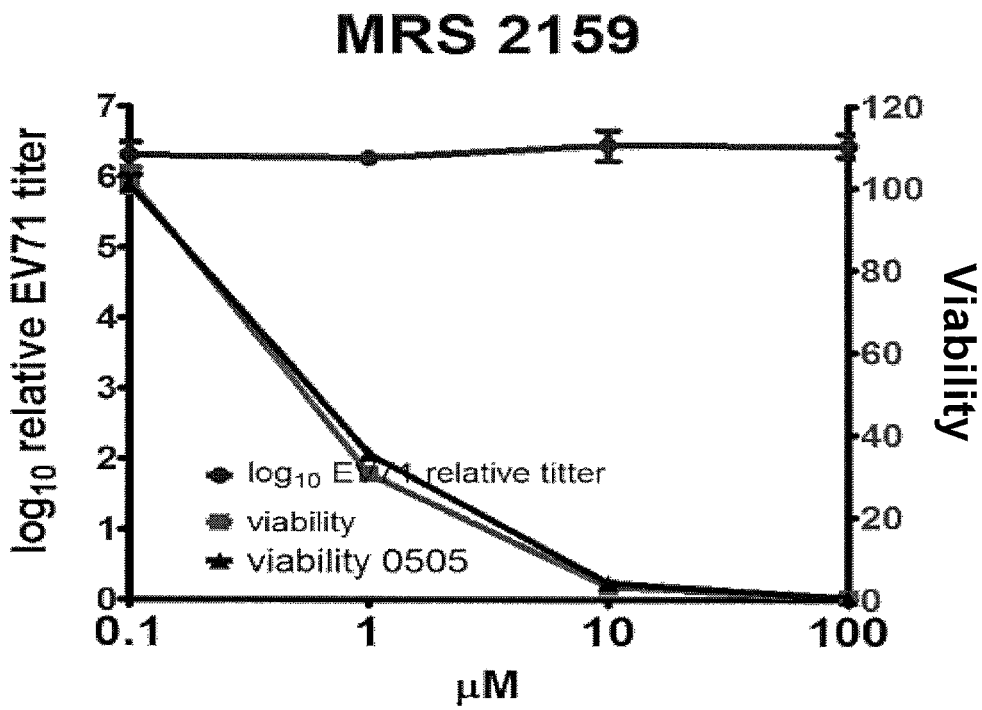
FIG. 21C shows inhibition by MRS 2159.
Figure 21D:
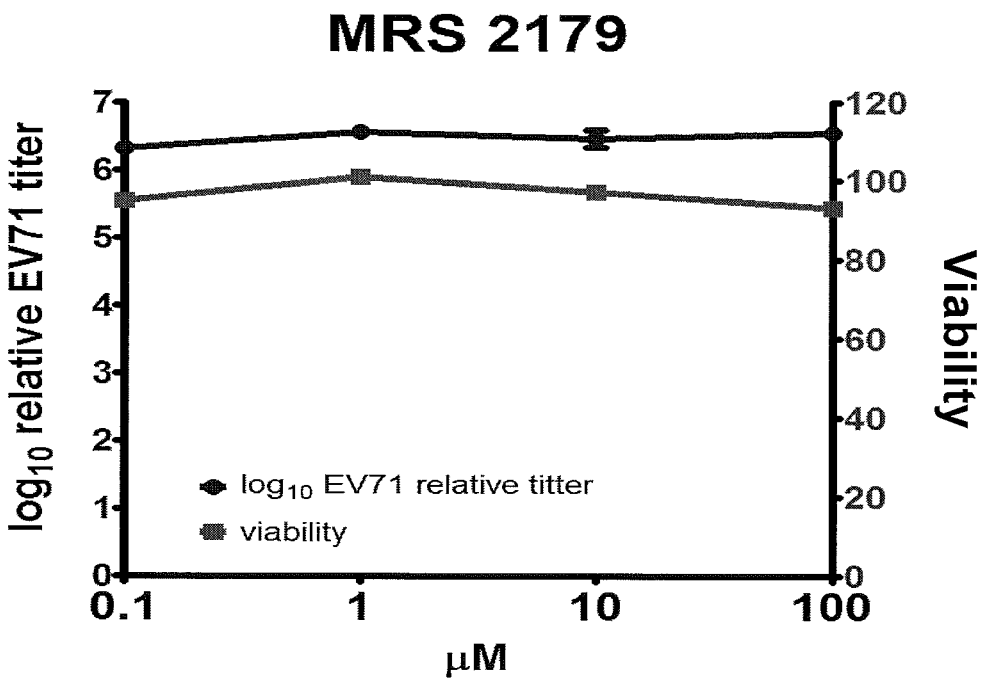
FIG. 21D shows inhibition by MRS 2179.
Figure 21E:
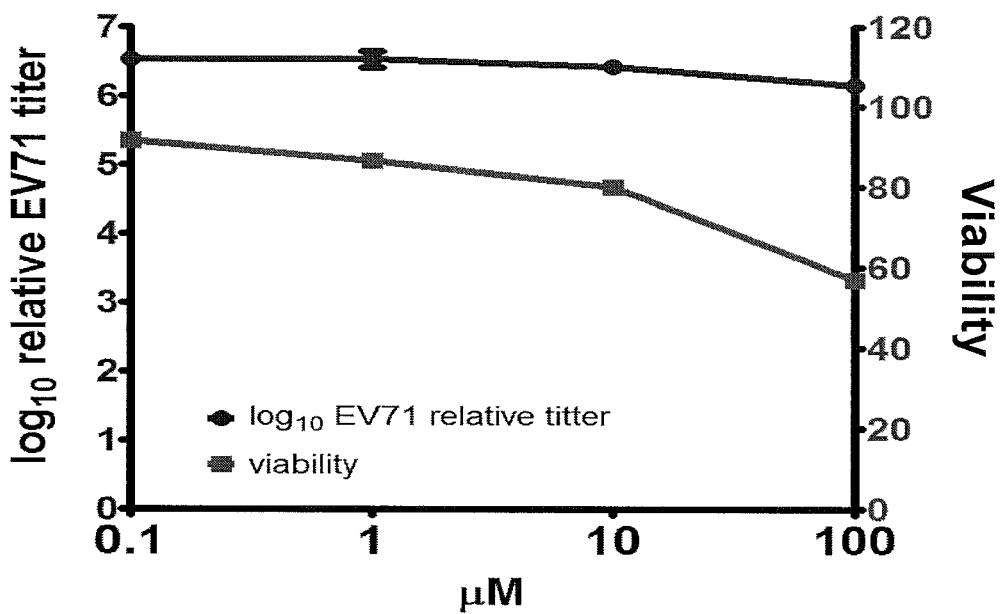
FIG. 21E shows inhibition by Ro 0437626.
Figure 21F:
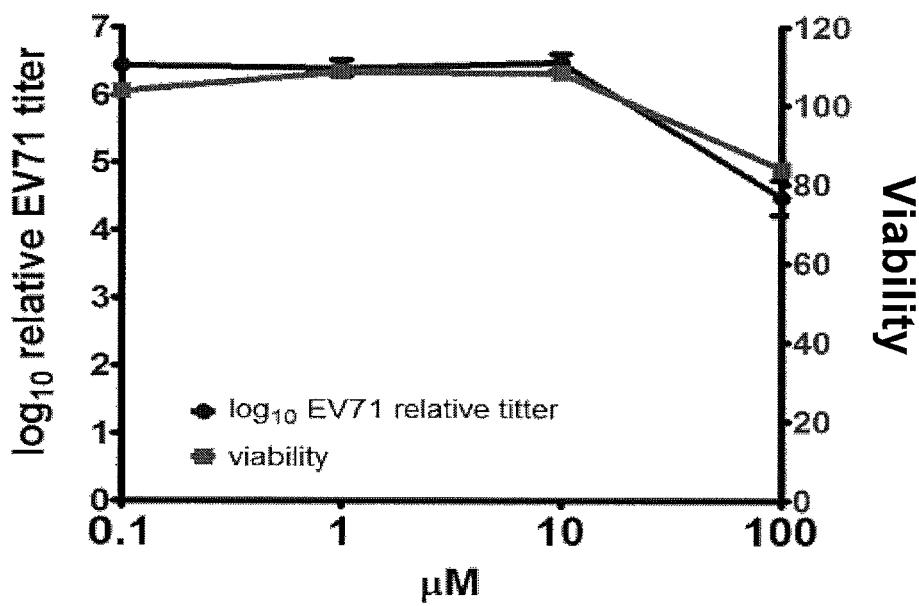
FIG. 21F shows inhibition by TNP-ATP.
Figure 21G:
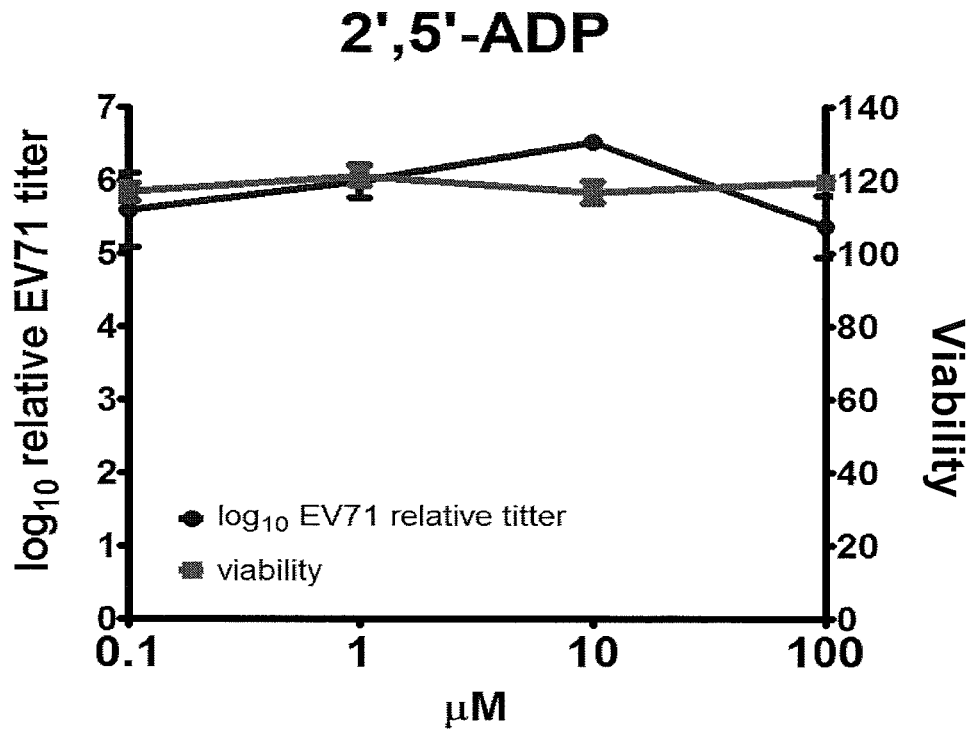
FIG. 21G shows inhibition by 2',5'-ADP.
Figure 21H:
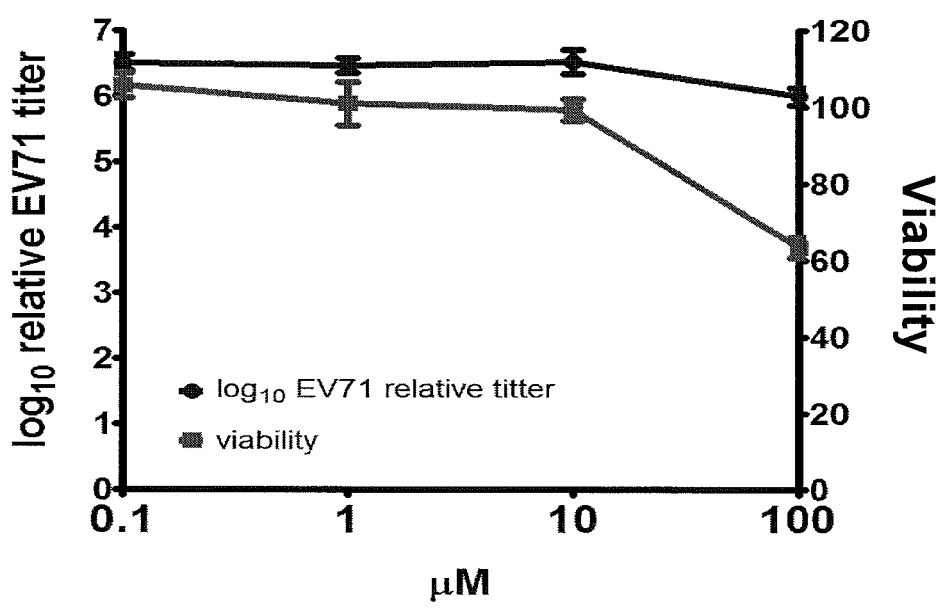
FIG. 21H shows inhibition by A 438079.
Figure 21I:
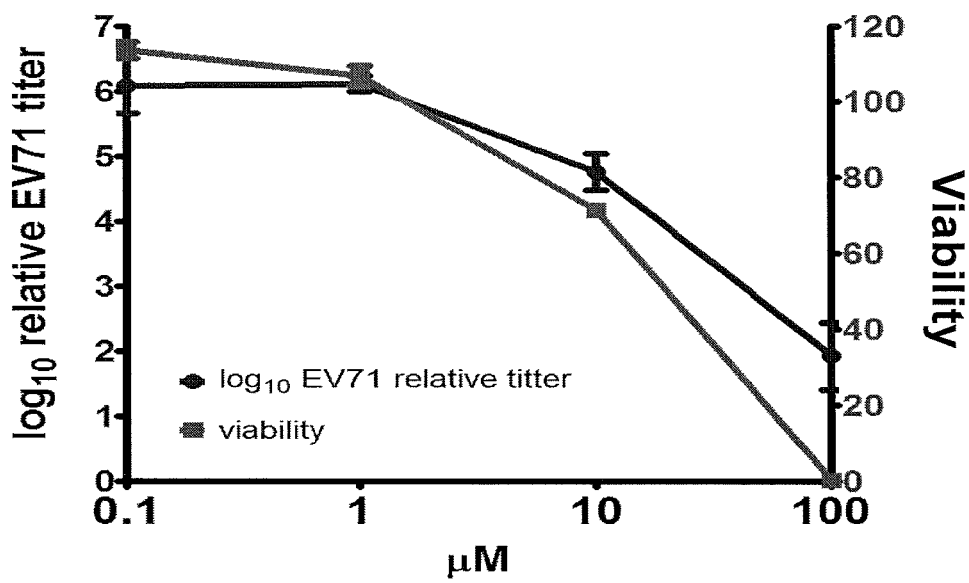
FIG. 21I shows inhibition by 5-BDBD.
Figure 21J:
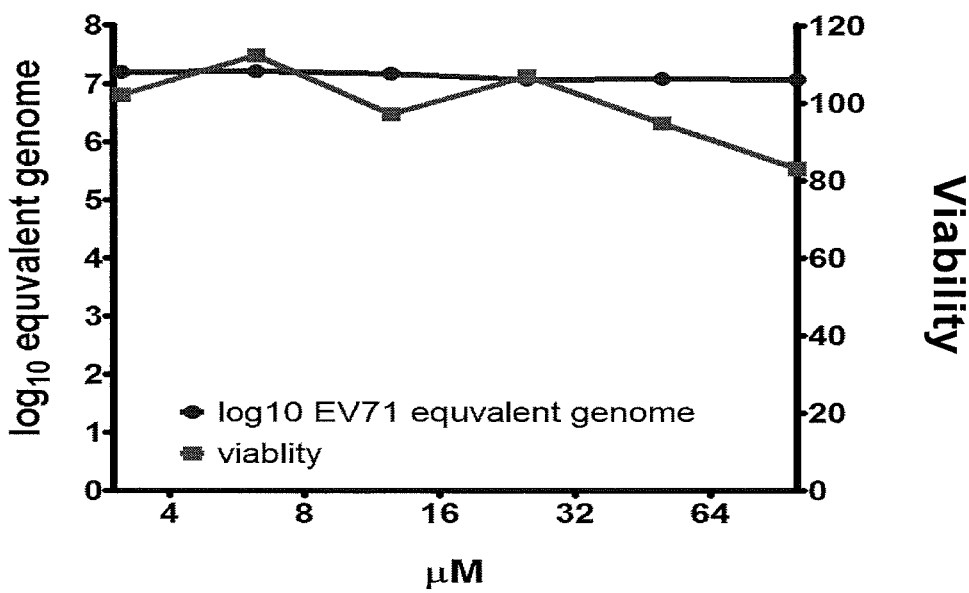
FIG. 21J shows inhibition by A 740003.
Figure 21K:
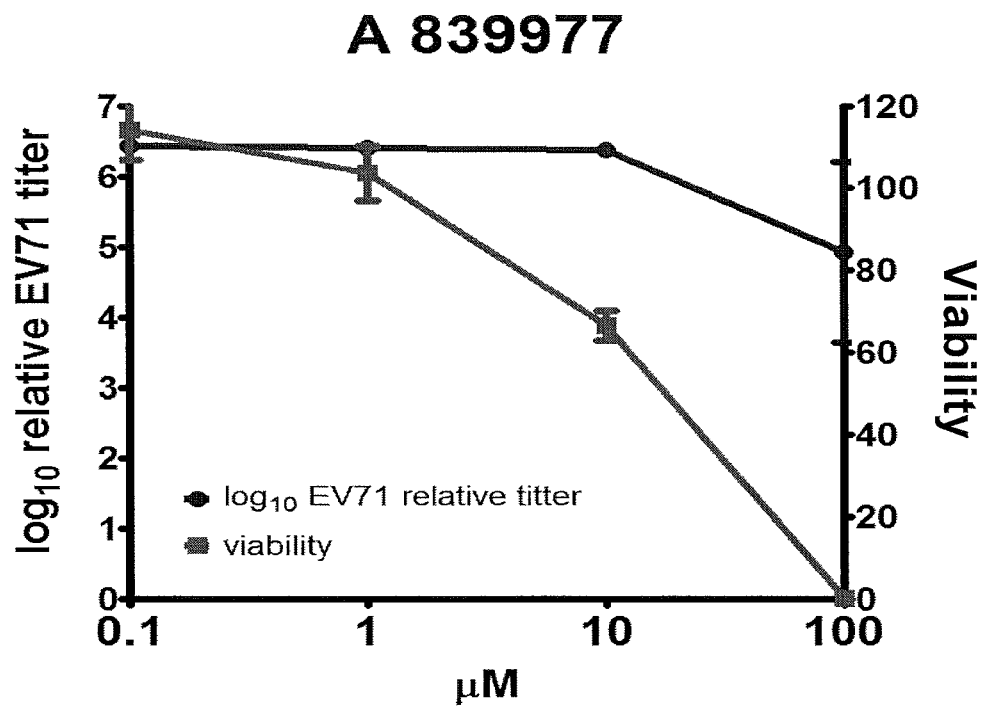
FIG. 21K shows inhibition by A 839977.
Figure 21L:
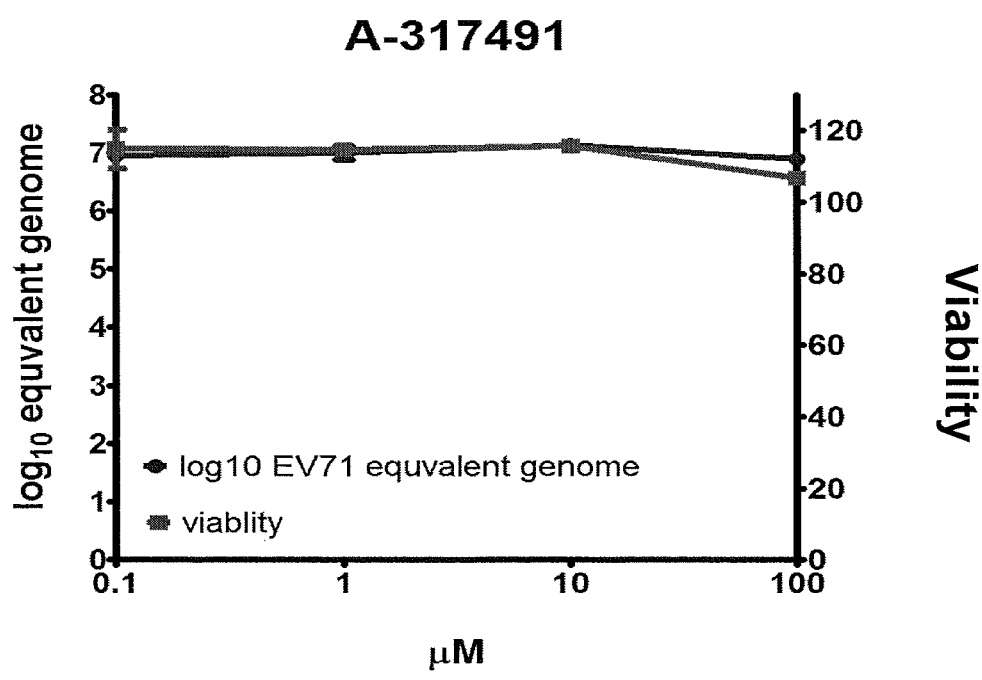
FIG. 21L shows inhibition by A-317491.
Figure 21M:
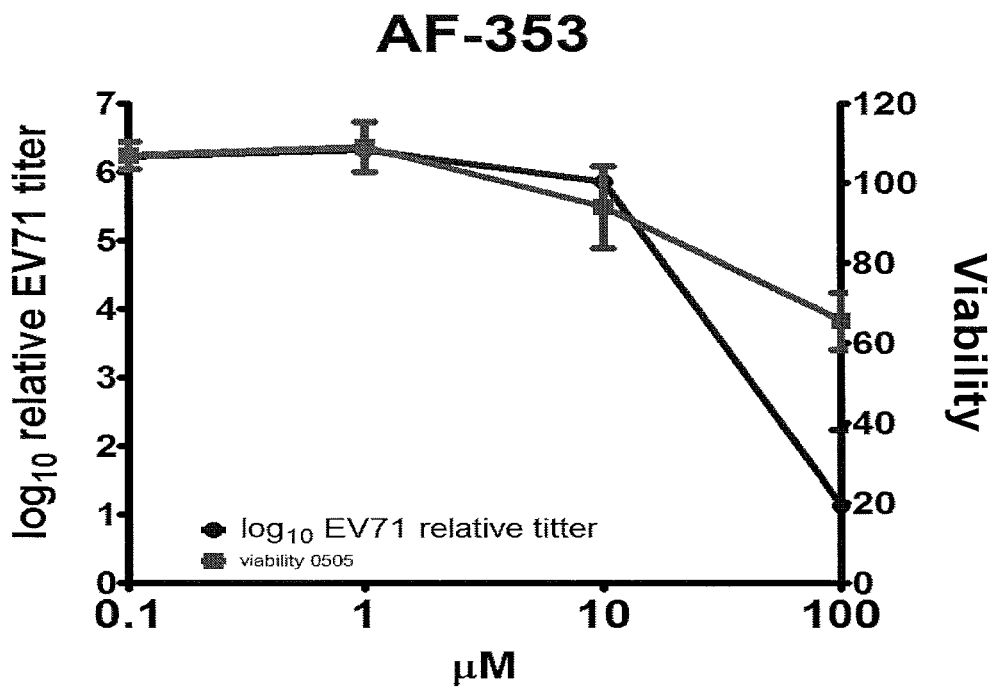
FIG. 21M shows inhibition by AF-353.
Figure 21N:
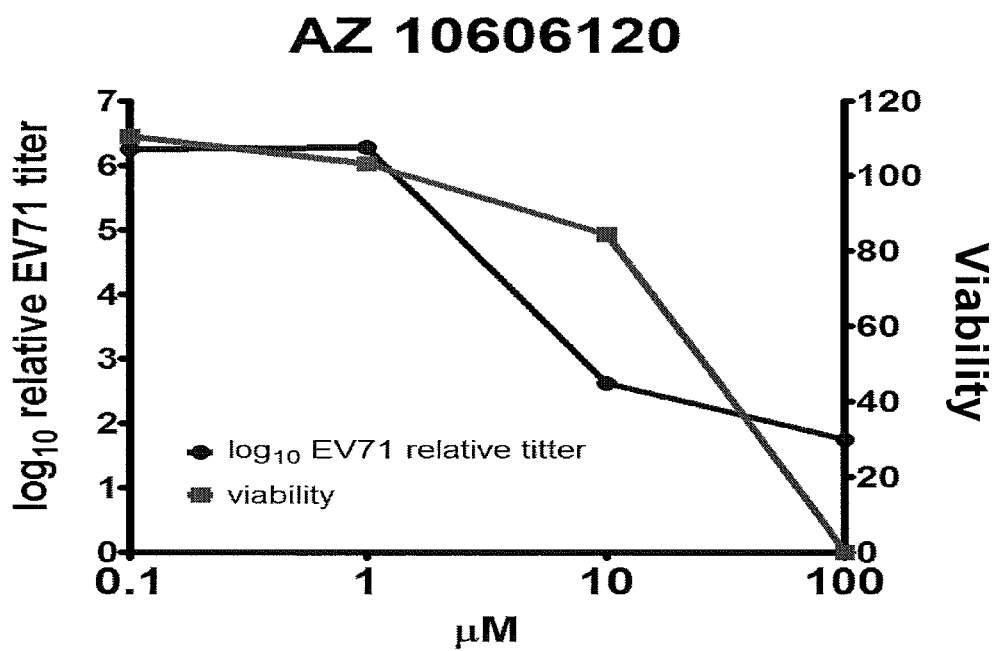
FIG. 21N shows inhibition by AZ 10606120.
Figure 21O:
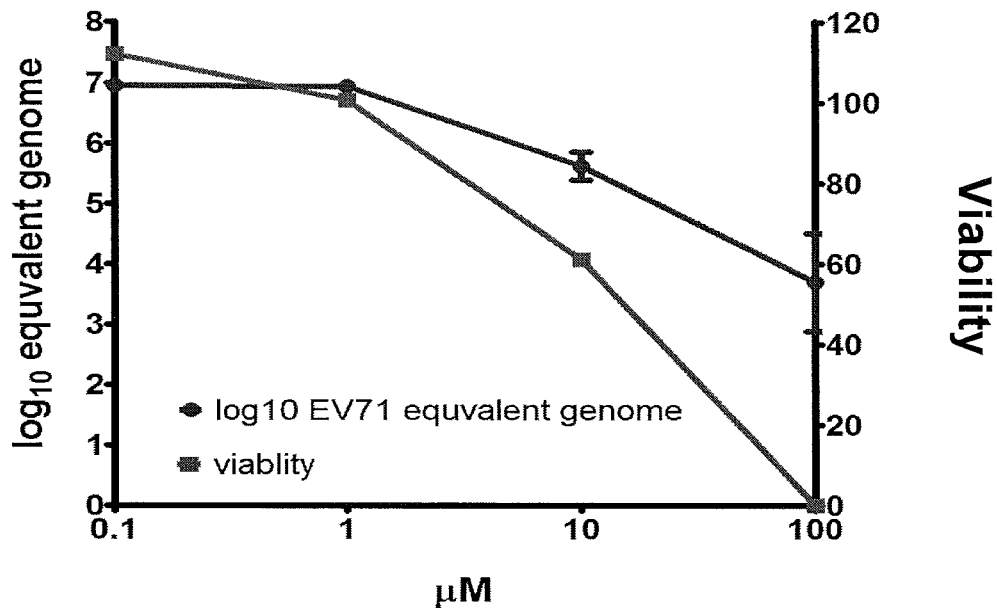
FIG. 21O shows inhibition by AZ 11645373.
Figure 21P:
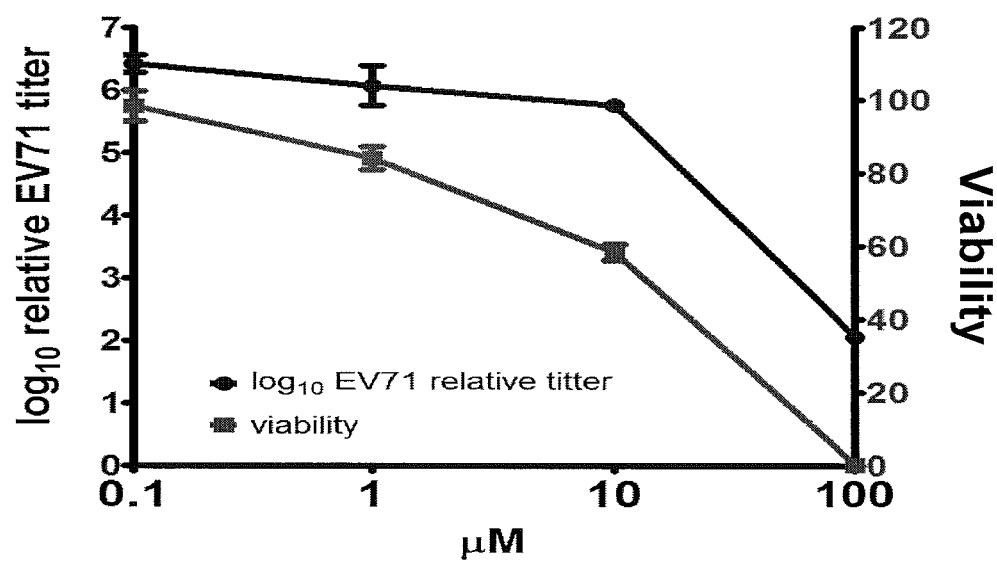
FIG. 21P shows inhibition by KN-62.
Figure 21Q:
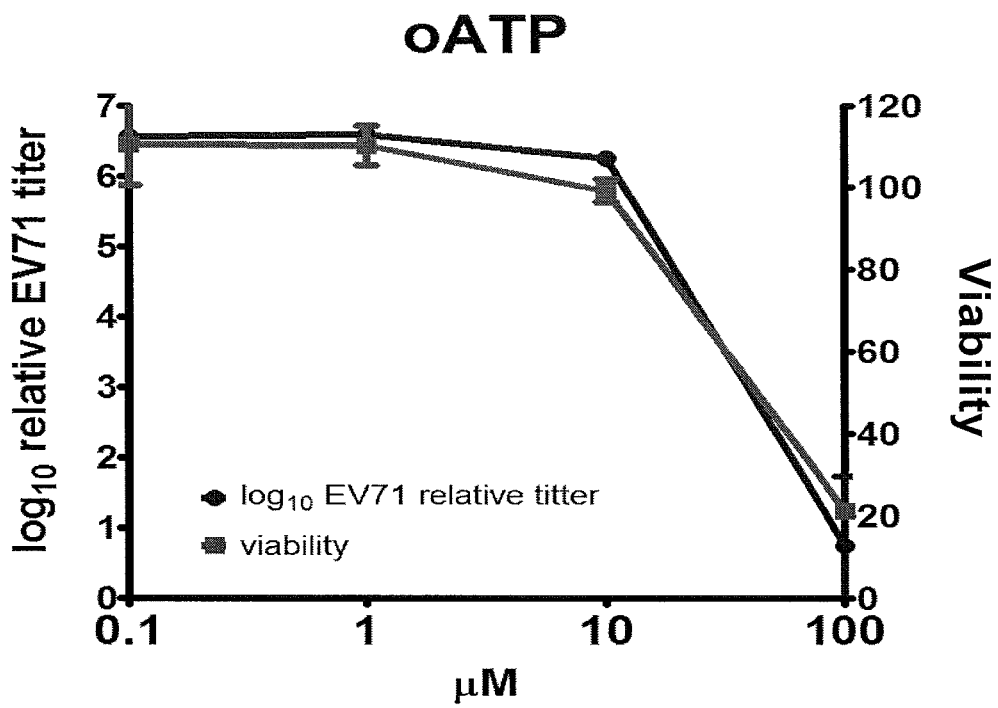
FIG. 21Q shows inhibition by oATP.
Figure 21R:
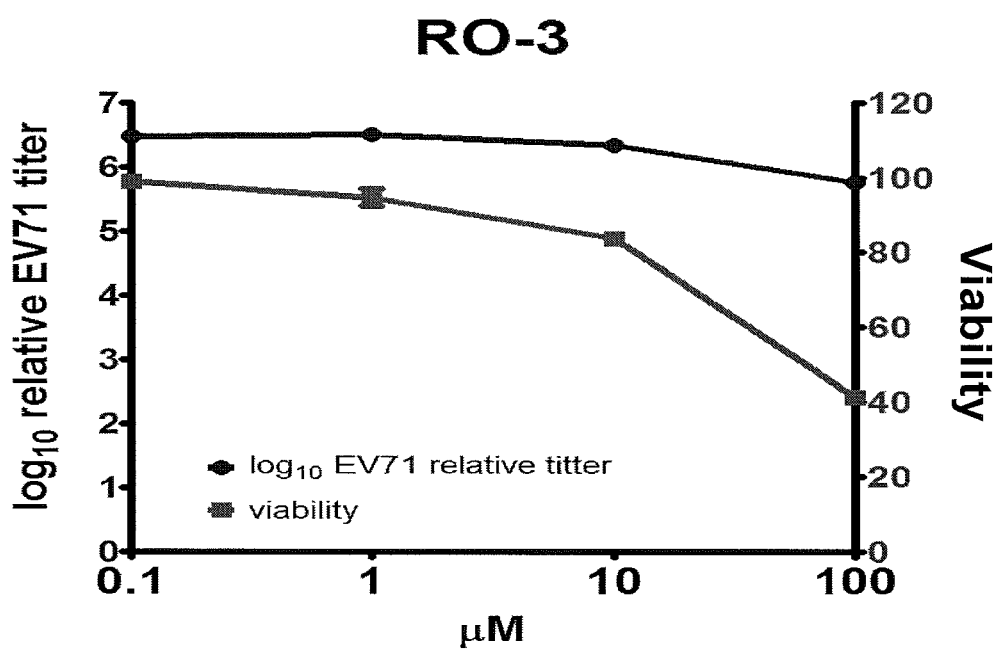
FIG. 21R shows inhibition by RO-3.
Figure 21U:
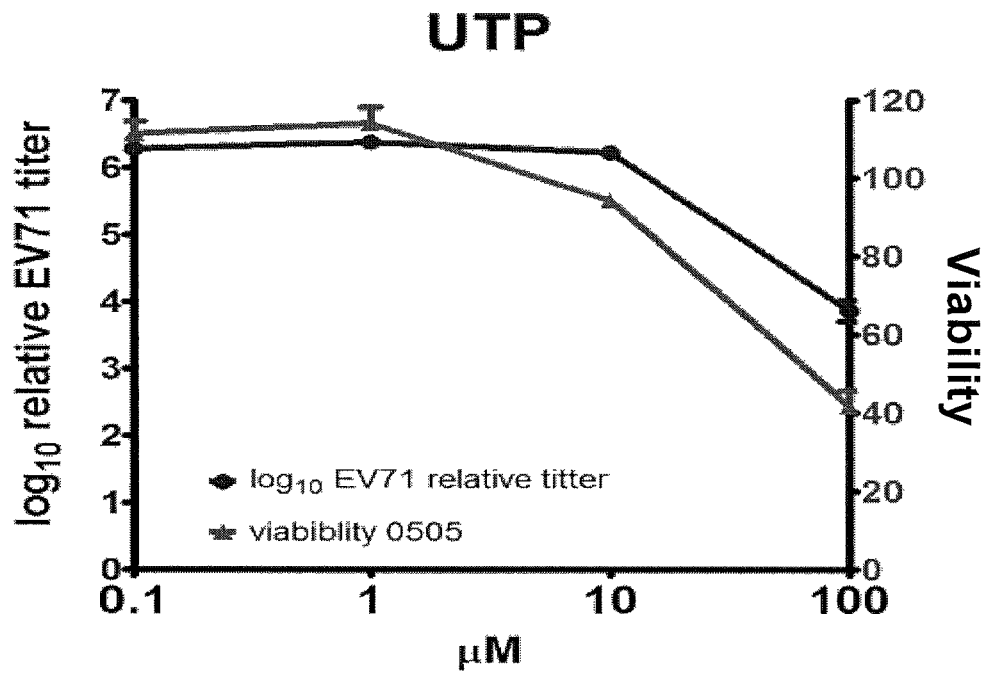
FIG. 21U shows inhibition by UTP.
Figure 21V:
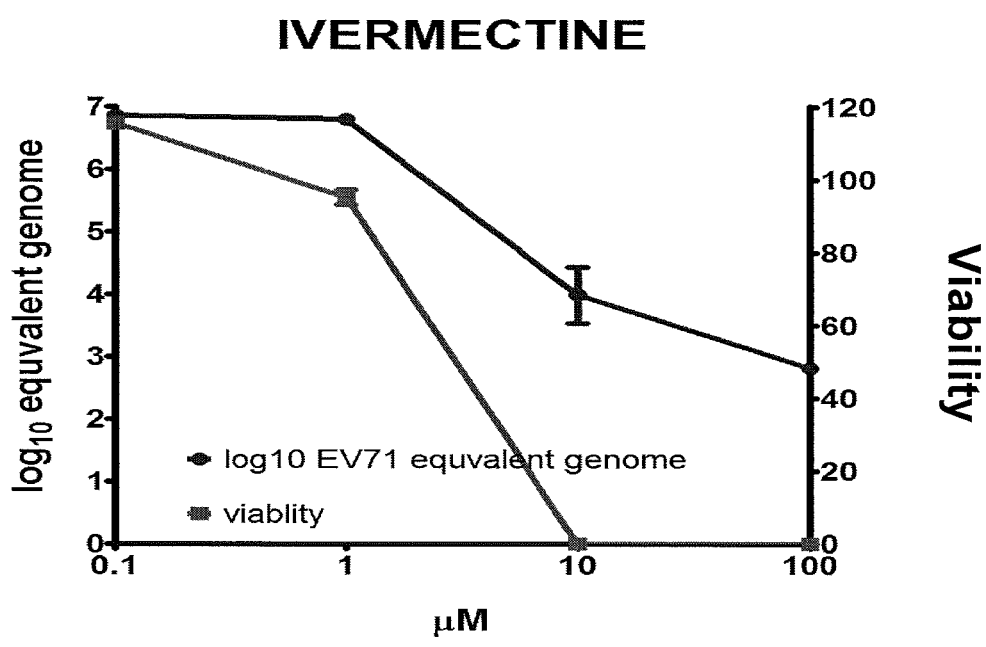
FIG. 21V shows inhibition by Ivermectine.
Figure 21W:
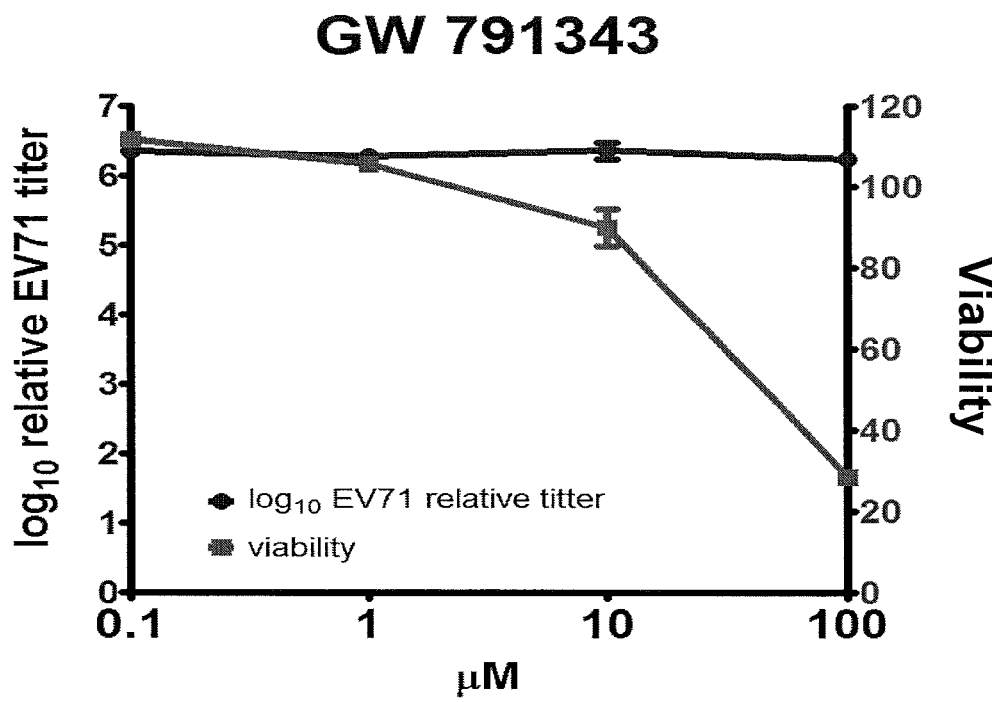
FIG. 21W shows inhibition by GW 791343.
Figure 21X:
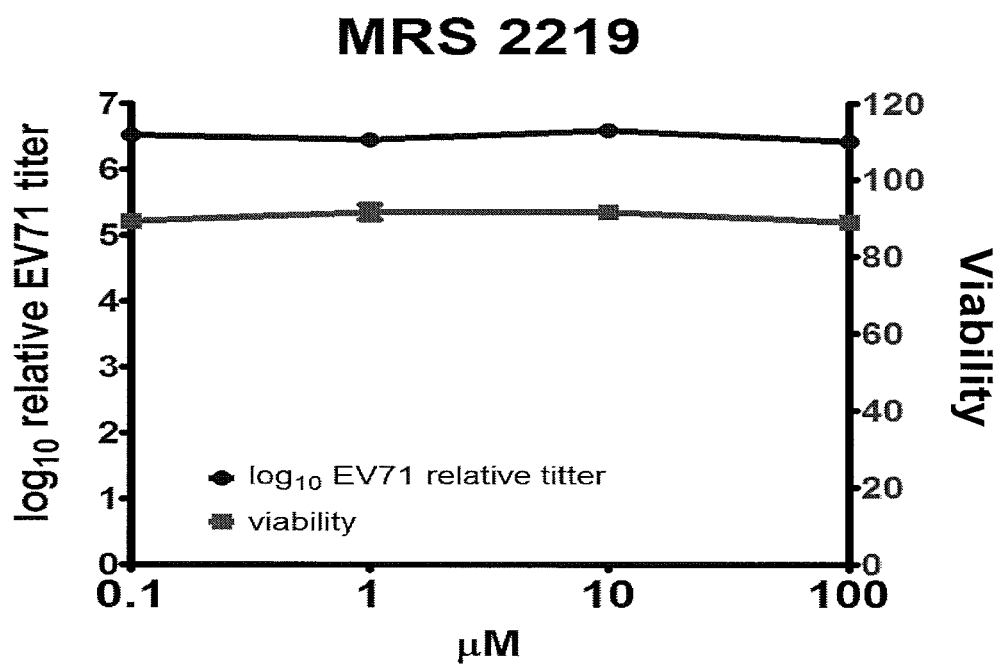

Effects of other antagonists and agonists on EV71 are shown in Table 9 and FIGS. 21A-X. FIG. 21A shows inhibition by NF110. FIG. 21B shows inhibition by BBG. FIG. 21C shows inhibition by MRS 2159. FIG. 21D shows inhibition by MRS 2179. FIG. 21E shows inhibition by Ro 0437626. FIG. 21F shows inhibition by TNP-ATP. FIG. 21G shows inhibition by 2',5'-ADP. FIG. 21H shows inhibition by A 438079. FIG. 21I shows inhibition by 5-BDBD. FIG. 21J shows inhibition by A 740003. FIG. 21K shows inhibition by A 839977. FIG. 21L shows inhibition by A-317491. FIG. 21M shows inhibition by AF-353. FIG. 21N shows inhibition by AZ 10606120. FIG. 21O shows inhibition by AZ 11645373. FIG. 21P shows inhibition by KN-62. FIG. 21Q shows inhibition by oATP. FIG. 21R shows inhibition by RO-3. FIG. 21S shows inhibition by Spinophin. FIG. 21T shows inhibition by bz ATP. FIG. 21U shows inhibition by UTP. FIG. 21V shows inhibition by Ivermectine. FIG. 21W shows inhibition by GW 791343. FIG. 21X shows inhibition by MRS 2219.

TABLE 9

Effects of other antagonists and agonists on EV71

| | P2X receptors | | | | | | | | | EV71 | |
|---|---|---|---|---|---|---|---|---|---|---|---|
| | 1 | 2 | 3 | 4 | 5 | 6 | 7 | P2Y | Heteromul timer | Log$_{10}$ reduction | IC$_{90}$ |
| Antagonists | | | | | | | | | | | |
| BBG | ✓ | ✓ | | | | | | ✓✓✓ | | NO | NO |
| MRS 2159 | ✓✓ | | | | | | | | | NO | NO |
| MRS 2179 | ✓ | | ✓ | | | | | ✓✓ P2Y1 | | NO | NO |
| NF 110 | ✓✓ | ✓ | ✓✓ | | | | | | | NO | NO |
| Ro 0437626 | ✓ | | | | | | | | | NO | NO |
| TNP-ATP | ✓✓✓ | | ✓✓✓ | | | | | | ✓✓✓ P2X2/3 | NO | NO |
| A-317491 | | | ✓✓ | | | | | | ✓✓ P2X2/3 | NO | NO |
| AF353 | | | ✓✓ | | | | | | ✓✓ P2X2/3 | NO | NO |
| RO-3 | | | ✓✓ | | | | | | ✓ P2X2/3 | NO | NO |
| Spinorphin | | | ✓✓✓ | | | | | | | NO | NO |
| 5-BDBD | | | | ✓ | | | | | | NO | NO |
| A 438079 | | | | | | | ✓✓ | | | NO | NO |
| A 740003 | | | | | | | ✓✓ | | | NO | NO |
| A 839977 | | | | | | | ✓✓ | | | NO | NO |
| AZ 10606120 | | | | | | | ✓✓✓ | | | NO | NO |
| AZ 11645373 | | | | | | | ✓✓ | | | NO | NO |
| KN-62 | | | | | | | ✓✓ | | | NO | NO |
| oATP | | | | | | | ✓✓ | | | NO | NO |
| 2',5'-ADP | | | | | | | | P2Y1 | | NO | NO |
| Agonists | | | | | | | | | | | |
| BzATP | ✓✓✓ | ✓✓ | ✓ | ✓✓✓ | ✓✓ | | ✓✓✓ | P2Y11 | | NO | NO |
| UTP | | | | ✓ | | | | | | NO | NO |

TABLE 9-continued

Effects of other antagonists and agonists on EV71

| | P2X receptors | | | | | | | | | EV71 | |
|---|---|---|---|---|---|---|---|---|---|---|---|
| | 1 | 2 | 3 | 4 | 5 | 6 | 7 | P2Y | Heteromul timer | $Log_{10}$ reduction | $IC_{90}$ |
| Modulator | | | | | | | | | | | |
| Ivermectin | | | | ✓✓✓ | | | | | | NO | NO |
| GW 791343 | | | | | | | ✓✓ | | | NO | |
| Response Potentiator | | | | | | | | | | | |
| MRS 2219 | ✓ | | | | | | | | | NO | NO |

In the Table, the "blank" indicates no data reported, "NO" indicates there is negative.
For Antagonists: ✓✓✓ activating concentration <10 nM, ✓✓ activating concentration 10 nM-300 nM, ✓ activating concentration >300 nM, —no activity.
For Agonists: ✓✓✓ activating concentration <1 µM, ✓✓ activating concentration 1-10 µM, ✓ activating concentration >10 µM.

Therefore, P2X1~6 subtype mRNAs are expressed in RD cells. In addition, a group of P2X receptor antagonists can inhibit EV71 replication in the infected RD cells. Combined with the association between P2X signal transduction and P2X abnormalities with diseases, it's suggested that P2X plays an important role in EV71 infection. There is a close relationship between the role of P2X and EV71 and the pathology of HFMD caused by EV71 infection;

In summary of the above examples, the following conclusions can be drawn:
(1) P2X receptor antagonist compound E02 can inhibit EV71 infection of RD cells;
(2) Compound E02 can reduce the ability of Coxsackie virus A16 to infect in RD cells;
(3) Compound E02 can reduce EV71 viral load in serum of ICR newborn mice;
(4) Compound E02 can reduce CVA16 viral load in brain, bone marrow, muscle, and serum of ICR newborn mice;
(5) E02 inhibits EV71 replication in rhesus monkeys in vivo and inhibits body temperature rise caused by EV71 in rhesus monkeys;
(6) P2X1-6 receptor subtype mRNAs can be detected in RD cells;
(7) Many P2X receptor antagonists can inhibit EV71 infection of RD cells.

All documents mentioned in the present invention are incorporated by reference in the present application, as if each reference was individually incorporated by reference. It should also be understood that, after reading the foregoing teachings of the present invention, those skilled in the art may make various modifications or changes to the present invention. These equivalents would similarly fall within the scope of the appended claims in the present application.

REFERENCES

Bonavia, A., M. Franti, et al. (2011). "Identification of broad-spectrum antiviral compounds and assessment of the druggability of their target for efficacy against respiratory syncytial virus (RSV)." Proceedings of the National Academy of Sciences 108(17): 6739-6744.
Burnstock, G. (2004). "Introduction: P2 Receptors." Current Topics in Medicinal Chemistry 4(8): 793-803.
Chong, J.-H., G.-G. Zheng, et al. (2010). "Abnormal expression of P2X family receptors in Chinese pediatric acute leukemias." Biochemical and Biophysical Research Communications 391(1): 498-504.
Coddou, C., Z. Yan, et al. (2011). "Activation and Regulation of Purinergic P2X Receptor Channels." Pharmacological Reviews 63(3): 641-683.
Daelemans, D., R. Pauwels, et al. (2011). "A time-of-drug addition approach to target identification of antiviral compounds." Nat. Protocols 6(6): 925-933.
Erb, L., Z. Liao, et al. (2006). "P2 receptors: intracellular signaling." Pflügers Archiv European Journal of Physiology 452(5): 552-562.
Geyer, J. R., R. Soto, et al. (2010). "AF-353, a novel, potent and orally bioavailable P2X3/P2X2/3 receptor antagonist." British Journal of Pharmacology 160(6): 1387-1398.
Han, J., X.-J. Ma, et al. (2010). "Long persistence of EV71 specific nucleotides in respiratory and feces samples of the patients with Hand-Foot-Mouth Disease after recovery." BMC Infectious Diseases 10(1): 178.
Huang, C.-C., C.-C. Liu, et al. (1999). "Neurologic Complications in Children with Enterovirus 71 Infection." New England Journal of Medicine 341(13): 936-942.
Khakh, B. S., G. Burnstock, et al. (2001). "International Union of Pharmacology. XXIV. Current Status of the Nomenclature and Properties of P2X Receptors and Their Subunits." Pharmacological Reviews 53(1): 107-118.
Khakh, B. S., W. R. Proctor, et al. (1999). "Allosteric Control of Gating and Kinetics at P2X4 Receptor Channels." The Journal of Neuroscience 19(17): 7289-7299.
Piqueur, M., W. Verstrepen, et al. (2009). "Improvement of a real-time RT-PCR assay for the detection of enterovirus RNA." Virology Journal 6(1): 95.
Rhoades, R. E., J. M. Tabor-Godwin, et al. (2011). "Enterovirus infections of the central nervous system." Virology 411(2): 288-305.
Solomon, T., P. Lewthwaite, et al. (2010). "Virology, epidemiology, pathogenesis, and control of enterovirus 71." The Lancet Infectious Diseases 10(11): 778-790.
Surprenant, A. and R. A. North (2009). "Signaling at Purinergic P2X Receptors." Annual Review of Physiology 71(1): 333-359.
Valera, S., N. Hussy, et al. (1994). "A new class of ligand-gated ion channel defined by P2X receptor for extracellular ATP." Nature 371(6497): 516-519.
Weng, K.-F., L.-L. Chen, et al. (2010). "Neural pathogenesis of enterovirus 71 infection." Microbes and Infection 12(7): 505-510.
Yan, X.-F., S. Gao, et al. "Epidemic characteristics of hand, foot, and mouth disease in Shanghai from 2009 to 2010: Enterovirus 71 subgenotype C4 as the primary causative agent and a high incidence of mixed infections with coxsackievirus A16." *Scandinavian Journal of Infectious Diseases* 0(0): 1-9.

Yang, F., L. Ren, et al. (2009). "Enterovirus 71 Outbreak in the People's Republic of China in 2008." *Journal of Clinical Microbiology* 47(7): 2351-2352.

Yang, Y., H. Wang, et al. (2009). "Neuropathology in 2 cases of fatal enterovirus type 71 infection from a recent epidemic in the People's Republic of China: a histopathologic, immunohistochemical, and reverse transcription polymerase chain reaction study." *Human Pathology* 40(9): 1288-1295.

Zhang, Y., D. Wang, et al. (2010). "Molecular Evidence of Persistent Epidemic and Evolution of Subgenotype B1 Coxsackievirus A16-Associated Hand, Foot, and Mouth Disease in China." *Journal of Clinical Microbiology* 48(2): 619-622.

Zhu, Z., S. Zhu, et al. (2010). "Retrospective seroepidemiology indicated that human enterovirus 71 and coxsackievirus A16 circulated wildly in central and southern China before large-scale outbreaks from 2008." *Virology Journal* 7(1): 300.

Chinese Ministry of Health (2010) Hand foot and mouth disease treatment guidelines (2010 edition.)

The invention claimed is:

1. A method for alleviating or treating hand foot and mouth disease, comprising: administering to a subject in need thereof a composition comprising a P2X receptor antagonist, wherein the P2X receptor antagonist is selected from the group consisting of: PPADS, iso-PPADS, PPNDS, Suramin, NF023, TNP-ATP, NF279, NF157, Evans Blue, an analog thereof, a derivative thereof, a pharmaceutically acceptable salt thereof, wherein a total daily dose of the P2X receptor antagonist is at 50-200 mg/kg body weight.

2. The method of claim 1, wherein the administering is by oral administration, intravenous injection, intramuscular injection, or inhalation.

3. A method for inhibiting infection by a positive-sense single-stranded RNA picornavirus that causes hand foot and mouth disease, comprising: administering to a subject in need thereof an effective amount of a P2X receptor antagonist, wherein the P2X receptor antagonist is selected from the group consisting of: PPADS, iso-PPADS, PPNDS, Suramin, NF023, TNT-ATP, NF279, NF157, Evans Blue, an analog thereof, a derivative thereof, and a pharmaceutically acceptable salt thereof, wherein a total daily dose of the P2X receptor antagonist is at 50-200 mg/kg body weight.

4. The method of claim 3, wherein the subject is a human, a monkey, or a mouse.

5. The method of claim 3, wherein the virus is an enterovirus or a Coxsackie virus.

6. The method of claim 3, wherein the virus is an enterovirus A.

7. The method of claim 3, wherein the virus is a human enterovirus 71.

8. The method of claim 3, wherein the virus is a Coxsackie virus.

9. The method of claim 1, wherein the P2X receptor antagonist is Suramin, total daily dose of Suramin is at 50 mg/kg body weight.

10. The method of claim 1, wherein total daily dose is divided into several doses for administration in a day.

11. The method of claim 3, wherein the P2X receptor antagonist is Suramin, total daily dose is of Suramin at 50 mg/kg body weight.

12. The method of claim 3, wherein total daily dose is divided into several doses for administration in a day.

13. The method of claim 1, wherein the subject is a human, a monkey, or a mouse.

14. The method of claim 3, wherein the administering is by oral administration, intravenous injection, intramuscular injection, or inhalation.

* * * * *

SEQUENCE LISTING

```
<160> NUMBER OF SEQ ID NOS: 19

<210> SEQ ID NO 1
<211> LENGTH: 18
<212> TYPE: DNA
<213> ORGANISM: Artificial Sequence
<220> FEATURE:
<223> OTHER INFORMATION: Synthetic

<400> SEQUENCE: 1
ccctgaatgc ggctaatc                                                 18

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
attgtcacca taagcagcca                                               20

<210> SEQ ID NO 3
<211> LENGTH: 28
<212> TYPE: DNA
<213> ORGANISM: Artificial Sequence
<220> FEATURE:
<223> OTHER INFORMATION: Synthetic

<400> SEQUENCE: 3
aaccgactac tttgggtgtc cgtgtttc                                      28

<210> SEQ ID NO 4
<211> LENGTH: 19
<212> TYPE: DNA
<213> ORGANISM: Artificial Sequence
<220> FEATURE:
<223> OTHER INFORMATION: Synthetic

<400> SEQUENCE: 4
gaaggtgaag gtcggagtc                                                19

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
gaagatggtg atgggatttc                                               20
```

```
<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
cctcttcgag tatgacacc                                                19

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
cagagacact gctgatgag                                                19

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
ctggacatgc tgggaaacg                                                19

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tgcccttgga gaagtggaat                                               20

<210> SEQ ID NO 10
<211> LENGTH: 17
<212> TYPE: DNA
<213> ORGANISM: Artificial Sequence
<220> FEATURE:
<223> OTHER INFORMATION: Synthetic

<400> SEQUENCE: 10
ggctcgacag cgtttct                                                  17

<210> SEQ ID NO 11
<211> LENGTH: 17
<212> TYPE: DNA
<213> ORGANISM: Artificial Sequence
<220> FEATURE:
<223> OTHER INFORMATION: Synthetic

<400> SEQUENCE: 11
tgccagcatt cccgtat                                                  17

<210> SEQ ID NO 12
<211> LENGTH: 18
<212> TYPE: DNA
<213> ORGANISM: Artificial Sequence
<220> FEATURE:
<223> OTHER INFORMATION: Synthetic
```

```
<400> SEQUENCE: 12
tgggatgtgg cggattat                                                   18

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
tacgcacctg cctgttgaga                                                 20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
tctttgcctg gtgcccgttg                                                 20

<210> SEQ ID NO 15
<211> LENGTH: 21
<212> TYPE: DNA
<213> ORGANISM: Artificial Sequence
<220> FEATURE:
<223> OTHER INFORMATION: Synthetic

<400> SEQUENCE: 15
atcacggagc ccagtcggaa g                                               21

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
ggaggacaaa gtatgaggag g                                               21

<210> SEQ ID NO 17
<211> LENGTH: 18
<212> TYPE: DNA
<213> ORGANISM: Artificial Sequence
<220> FEATURE:
<223> OTHER INFORMATION: Synthetic

<400> SEQUENCE: 17
gaatgggttg gcaagtgg                                                   18

<210> SEQ ID NO 18
<211> LENGTH: 18
<212> TYPE: DNA
<213> ORGANISM: Artificial Sequence
<220> FEATURE:
<223> OTHER INFORMATION: Synthetic

<400> SEQUENCE: 18
cgtggagaag tgaagaag                                                   18

<210> SEQ ID NO 19
<211> LENGTH: 19
```

```
<212> TYPE: DNA
<213> ORGANISM: Artificial Sequence
<220> FEATURE:
<223> OTHER INFORMATION: Synthetic

<400> SEQUENCE: 19
tcggtcagag gaacagagc                                                        19
```